United States Patent
Bruestle

(10) Patent No.: US 11,717,265 B2
(45) Date of Patent: Aug. 8, 2023

(54) METHODS AND SYSTEMS FOR AN ACOUSTIC ATTENUATING MATERIAL

(71) Applicant: General Electric Company, Schenectady, NY (US)

(72) Inventor: Reinhold Bruestle, Frankenburg am Hausruck (AT)

(73) Assignee: General Electric Company, Schenectady, NY (US)

( * ) Notice: Subject to any disclaimer, the term of this patent is extended or adjusted under 35 U.S.C. 154(b) by 1243 days.

(21) Appl. No.: 16/206,584

(22) Filed: Nov. 30, 2018

(65) Prior Publication Data

US 2020/0170620 A1    Jun. 4, 2020

(51) Int. Cl.
| | |
|---|---|
| *A61B 8/00* | (2006.01) |
| *G10K 11/00* | (2006.01) |
| *B06B 1/06* | (2006.01) |
| *G01S 7/52* | (2006.01) |
| *A61B 18/00* | (2006.01) |

(52) U.S. Cl.
CPC .......... *A61B 8/4494* (2013.01); *B06B 1/0685* (2013.01); *G01S 7/52079* (2013.01); *G10K 11/002* (2013.01); *A61B 2018/00089* (2013.01); *B06B 2201/76* (2013.01)

(58) Field of Classification Search
CPC . B06B 1/0685; G01S 7/52079; G10K 11/002; A61B 8/4494; B33Y 10/00
See application file for complete search history.

(56) References Cited

U.S. PATENT DOCUMENTS

| | | | | |
|---|---|---|---|---|
| 4,262,399 A | * | 4/1981 | Cady ..................... | B06B 1/0292 438/739 |
| 5,267,221 A | * | 11/1993 | Miller ................... | B06B 1/0622 367/176 |
| 5,648,942 A | * | 7/1997 | Kunkel, III .......... | G10K 11/002 367/176 |
| 6,236,144 B1 | * | 5/2001 | Millar ................... | B06B 1/0685 310/334 |
| 6,258,034 B1 | * | 7/2001 | Hanafy ................. | B06B 1/0685 29/25.35 |
| 6,271,620 B1 | * | 8/2001 | Ladabaum ............. | G01H 11/06 310/365 |
| 6,865,140 B2 | | 3/2005 | Thomenius et al. | |

(Continued)

FOREIGN PATENT DOCUMENTS

| | | | | |
|---|---|---|---|---|
| CA | 2896532 A1 | * | 7/2014 | ........... B06B 1/0651 |
| CN | 101675468 B | | 11/2012 | |

(Continued)

OTHER PUBLICATIONS

CN application 201911210520.4 filed Nov. 28, 2019—Office Action dated Jun. 28, 2022; 11 pages.

(Continued)

*Primary Examiner* — Oommen Jacob
(74) *Attorney, Agent, or Firm* — McCoy Russell LLP

(57) ABSTRACT

Various methods and systems are provided for fabricating a backing material for an acoustic probe. In one example, the backing material may include an additively manufactured meta-structure formed from layers of a tessellation pattern. A geometry of the tessellation pattern and an alignment of the layers may affect acoustic properties of the backing material.

10 Claims, 15 Drawing Sheets

(56) References Cited

U.S. PATENT DOCUMENTS

| | | | |
|---|---|---|---|
| 8,992,703 | B2 | 3/2015 | O'Neill et al. |
| 9,296,129 | B2 | 3/2016 | Pallari |
| 9,943,287 | B2 * | 4/2018 | Sudol .................... A61B 8/4494 |
| 10,314,562 | B2 * | 6/2019 | Song .................... A61B 8/4444 |
| 2005/0043625 | A1 * | 2/2005 | Oliver .................. A61B 8/4483 600/459 |
| 2006/0043839 | A1 * | 3/2006 | Wildes ................. G10K 11/004 310/327 |
| 2006/0147332 | A1 | 7/2006 | Jones et al. |
| 2008/0243001 | A1 * | 10/2008 | Oakley ................ A61B 8/4281 600/459 |
| 2011/0014081 | A1 | 1/2011 | Jones et al. |
| 2012/0238880 | A1 * | 9/2012 | Davidsen ............. G10K 11/002 600/459 |
| 2013/0088122 | A1 | 4/2013 | Krohn et al. |
| 2015/0173712 | A1 * | 6/2015 | Song .................... A61B 8/4483 29/25.35 |
| 2016/0167132 | A1 | 6/2016 | Panat |
| 2017/0277168 | A1 | 9/2017 | Tanaka |
| 2019/0178849 | A1 * | 6/2019 | Abraham ............... B33Y 80/00 |
| 2020/0170620 | A1 * | 6/2020 | Bruestle ............... G10K 11/002 |

FOREIGN PATENT DOCUMENTS

| | | |
|---|---|---|
| CN | 104720847 B | 4/2020 |
| EP | 3181273 A1 | 6/2017 |
| WO | 2017117527 A1 | 7/2017 |

OTHER PUBLICATIONS

Office Action reference CN101675468; English Abstract, Espacenet search results dated Sep. 28, 2022; 1 page.

* cited by examiner

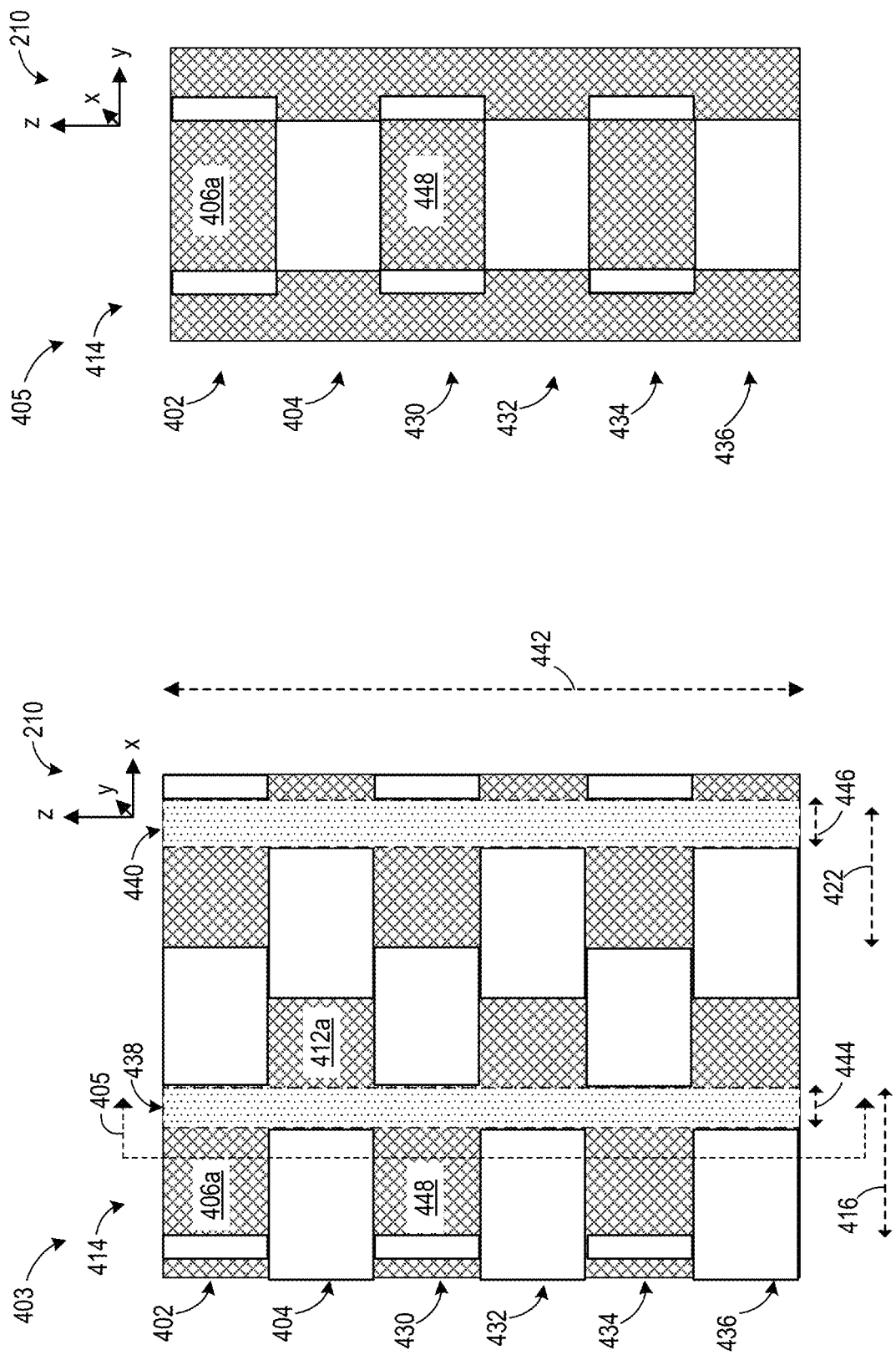

METHODS AND SYSTEMS FOR AN ACOUSTIC ATTENUATING MATERIAL

FIELD

Embodiments of the subject matter disclosed herein relate to methods and systems for manufacturing a backing material for an ultrasound transducer.

BACKGROUND

Ultrasound, for medical or industrial applications, is an imaging modality that employs ultrasound waves to probe the acoustic properties of a target object (e.g., the body of a patient) and produce a corresponding image. A resolution, intensity, and/or focus of an ultrasonic signal output by a transducer of an ultrasound probe of an ultrasound imaging system may be tuned by adjusting a plurality of components of the ultrasound probe. The plurality of components may include a backing configured to control a bandwidth, temporal resolution, and a sensitivity of the ultrasound probe. A material from which the backing is formed may have an acoustic impedance lower than that of an active element of the transducer that generates the ultrasonic signal and may be configured with acoustic attenuating properties. Furthermore, the backing material may be thermally conductive to aid in dissipating heat generated in the ultrasound probe.

BRIEF DESCRIPTION

In one embodiment, an ultrasound transducer comprises an element for generating ultrasonic waves and a backing arranged behind the element, the backing including a layer having a tessellation pattern.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 4B shows a first cross-section of the second tessellation pattern.

FIG. 4C shows a second cross-section of the second tessellation pattern.

DETAILED DESCRIPTION

Figure 1:
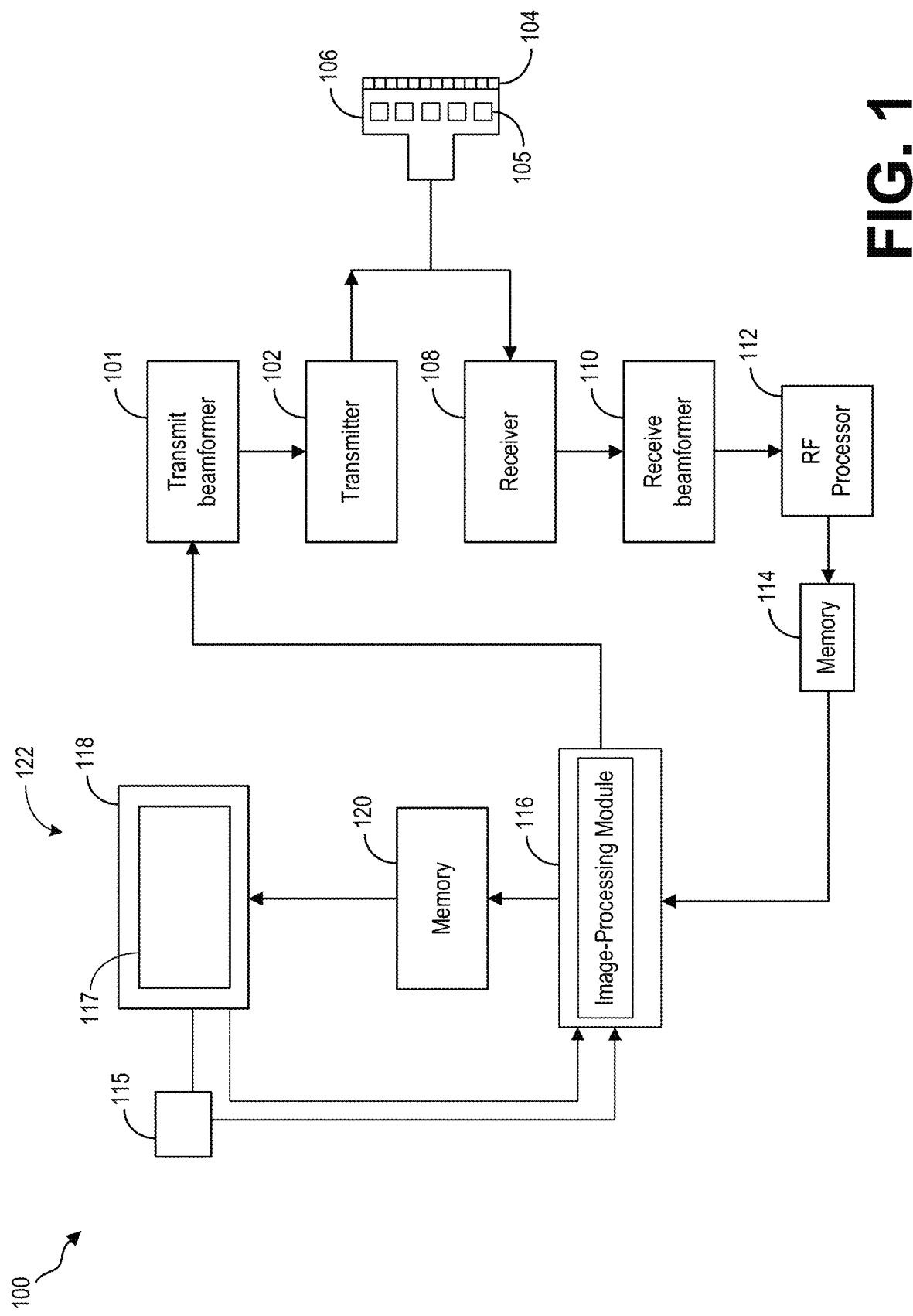
FIG. 1 shows an example ultrasonic imaging system according to an embodiment of the invention.
Figure 2:
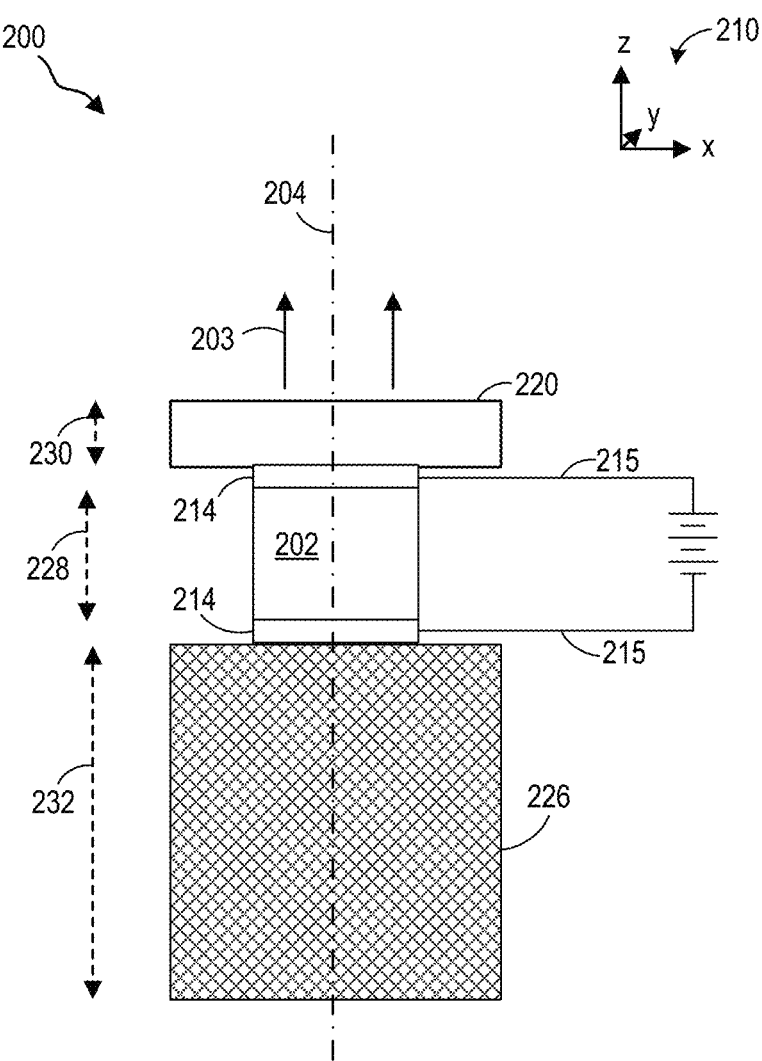
FIG. 2 shows an example of an acoustic stack of an ultrasound transducer.
Figure 8A:
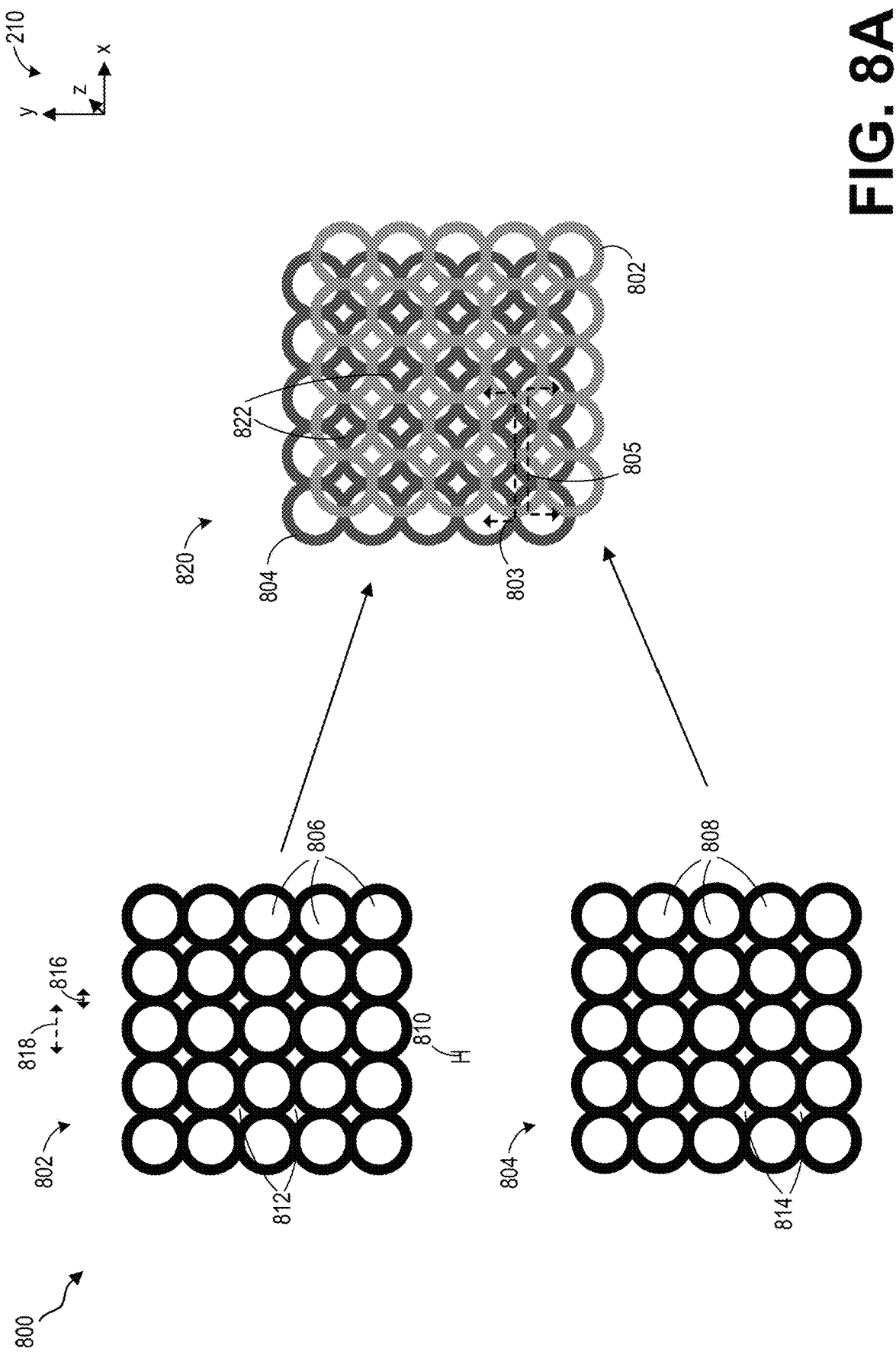
FIG. 8A shows an example of a sixth tessellation pattern for a backing material of an ultrasound probe.
Figure 8C:
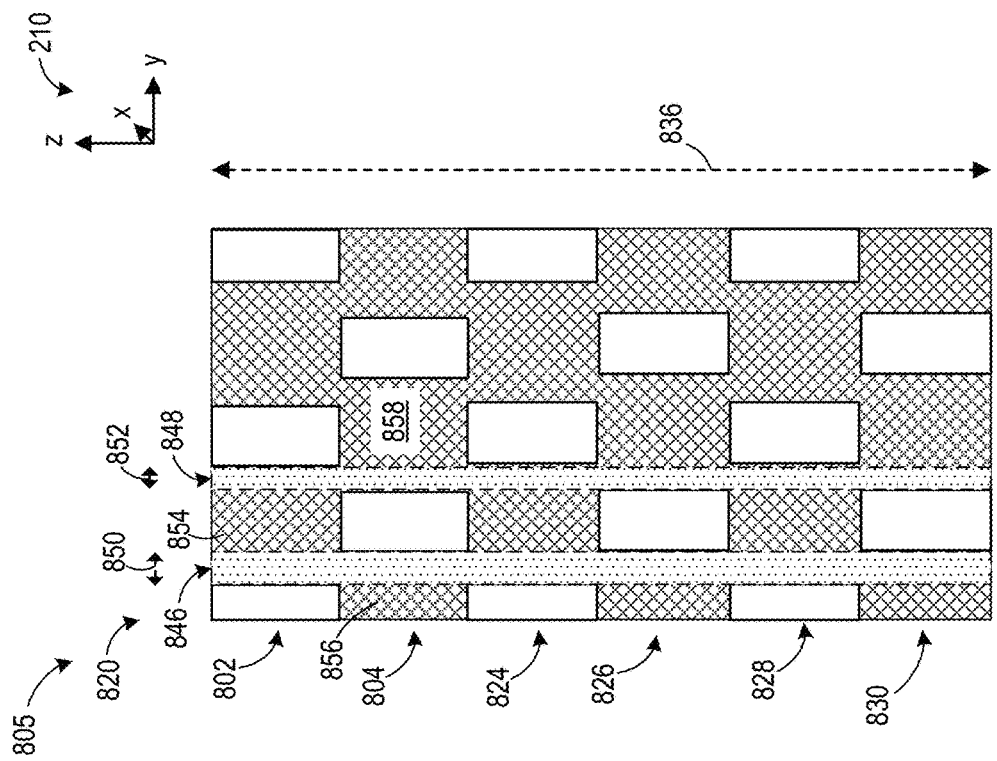
FIG. 8C shows a second cross-section of the sixth tessellation pattern.
Figure 8B:
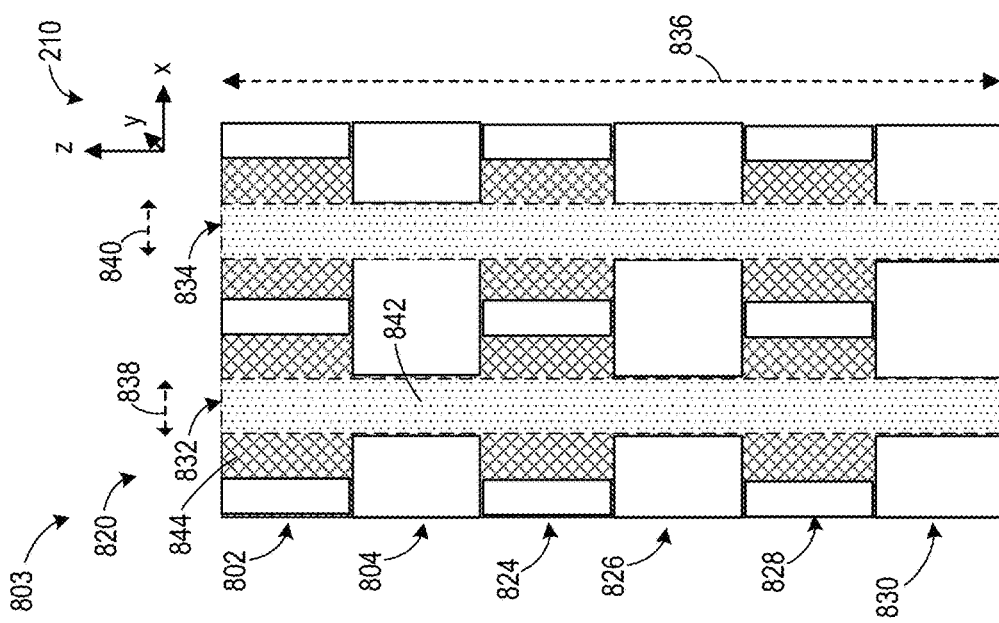
FIG. 8B shows a first cross-section of the sixth tessellation pattern.
Figure 9:
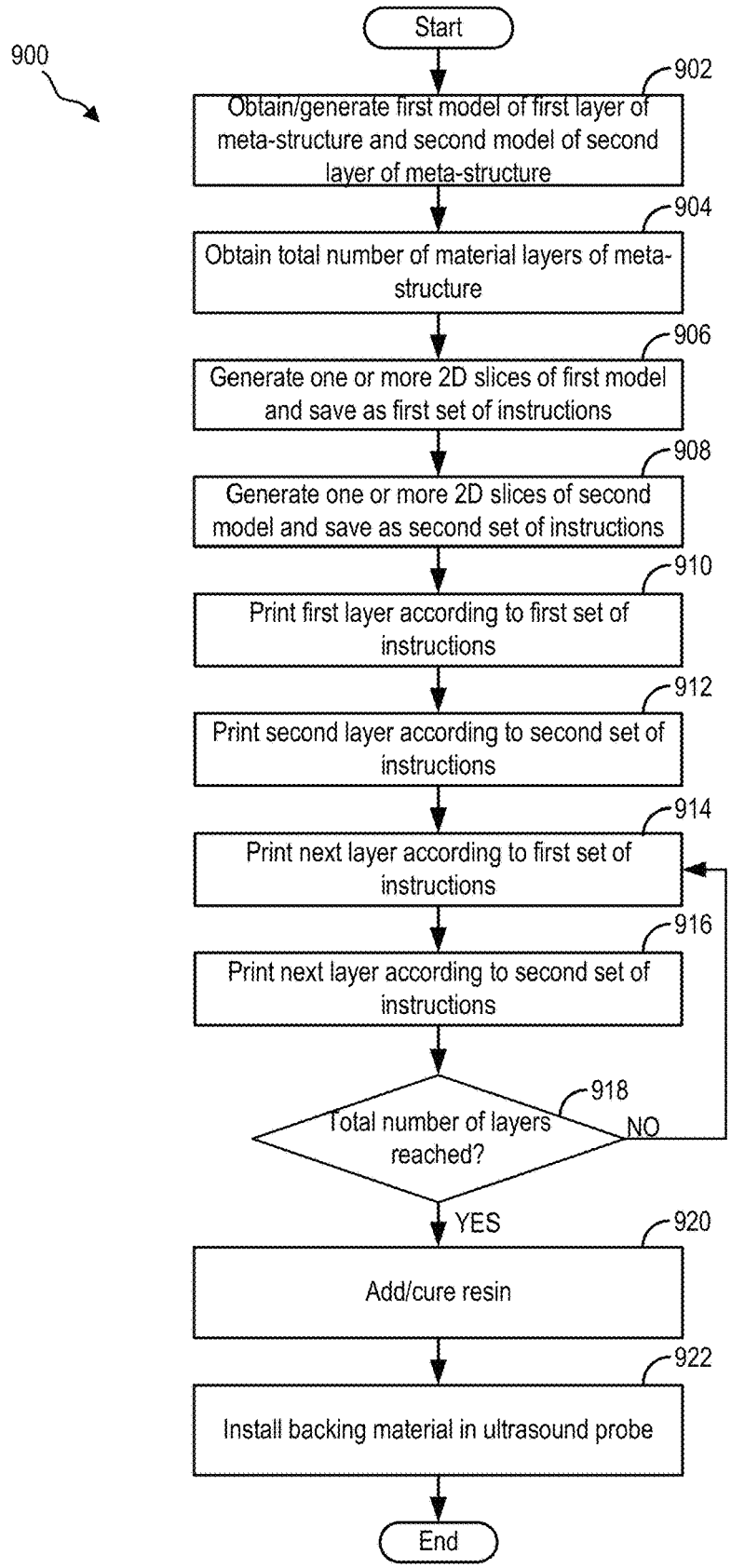
FIG. 9 shows an example of a method for manufacturing a backing material.

The following description relates to various embodiments of an ultrasound probe, such as the ultrasound probe shown in FIGS. 1 and 2. The ultrasound probe may be included in an ultrasound system imaging system, such as the ultrasound imaging system shown in FIG. 1. In particular, systems and methods are provided for forming a backing material for one or more transducers of the ultrasound probe. An example of an acoustic stack of ultrasound probe is depicted in FIG. 2, showing components of the probe including the backing material. The backing material may be at least partially formed by additive manufacturing and configured to attenuate and diffuse acoustic waves in the ultrasound probe. The backing material may be adapted with tessellated layers that include a repeating pattern of a geometrically shaped void. The geometric shape of the void used in the pattern may affect an efficiency of the backing material in attenuating acoustic waves. Examples of different geometric shapes that may be used in the tessellation pattern are shown in FIGS. 3A-8C, which illustrate patterns based on hexagons, squares, triangles, and circles. FIGS. 3A-8C include top down views of meta-structures formed from each of the tessellation patterns as well as cross-sectional views. The meta-structures may be one component of the backing material with a first set of acoustic properties, providing a framework or scaffold for a second component with a second set of acoustic properties that fills a plurality of cells in the meta-structure. An example of a method for fabricating the backing material is shown in FIG. 9, the method including use of additive manufacturing to generate a scaffold of the backing material.

FIGS. 2-8C show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Turning now to FIG. 1, a block diagram of an ultrasound imaging system 100 according to one embodiment is illustrated. As shown, the system 100 includes multiple components. The components may be coupled to one another to form a single structure, may be separate but located within a common room, or may be remotely located with respect to one another. For example, one or more of the modules described herein may operate in a data server that has a distinct and remote location with respect to other components of the system 100, such as a probe and user interface. Optionally, in the case of ultrasound systems, the system 100 may be a unitary system that is capable of being moved (e.g., portably) from room to room. For example, the system 100 may include wheels or be transported on a cart.

In the illustrated embodiment, the system 100 includes a transmit beamformer 101 and transmitter 102 that drives an array of elements 104, for example, piezoelectric crystals, within a diagnostic ultrasound probe 106 (or transducer) to emit pulsed ultrasonic signals into a body or volume (not shown) of a subject. Furthermore, the probe is outfitted with one or more actuators 105 capable of receiving signals from a system controller 116, as described further below, in order to output tactile feedback to the user. The elements 104, the one or more actuators 105, and the probe 106 may have a variety of geometries.

The probe 106 may also include additional components, such as a metal casing, an acoustic matching layer, an acoustic lens, and a backing material. Each component may have a specific role in moderating an emission and/or reception of ultrasonic waves within the probe 106. For example, the backing material may increase an axial resolution of the transmitted ultrasonic signals by dampening excessive vibrations in the probe 106 arising oscillation of array of elements 104 when a potential is applied. Components of the probe are described further below with reference to FIG. 2 and details of the backing material are provided in the following descriptions of FIGS. 3A-8C.

The ultrasonic signals emitted by the elements 104 are back-scattered from structures in the body, for example, blood vessels and surrounding tissue, to produce echoes that return to said elements 104. The echoes are received by a receiver 108. The received echoes are provided to a beamformer 110 that performs beamforming and outputs an RF signal. The RF signal is then provided to an RF processor 112 that processes the RF signal. Alternatively, the RF processor 112 may include a complex demodulator (not shown) that demodulates the RF signal to form IQ data pairs representative of the echo signals. The RF or IQ signal data may then be provided directly to a memory 114 for storage (for example, temporary storage).

The system controller (e.g., electronic controller) 116 of the system 100 includes a plurality of modules, which may be part of a single processing unit (e.g., processor) or distributed across multiple processing units. The system controller 116 is configured to control operation of the system 100. For example, the system controller 116 may include an image-processing module that receives image data (e.g., ultrasound signals in the form of RF signal data or IQ data pairs) and processes image data. For example, the image-processing module may process the ultrasound signals to generate slices or frames of ultrasound information (e.g., ultrasound images) for displaying to the operator. In system 100, the image-processing module may be configured to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler module, C-scan, and elastography. The generated ultrasound images may be two-dimensional (2D) or three-dimensional (3D). When multiple two-dimensional (2D) images are obtained, the image-processing module may also be configured to stabilize or register the images.

Acquired ultrasound information may be processed in real-time during an imaging session (or scanning session) as the echo signals are received. Additionally or alternatively, the ultrasound information may be stored temporarily in the memory 114 during an imaging session and processed in less than real-time in a live or off-line operation. An image memory 120 is included for storing processed slices of acquired ultrasound information that are not scheduled to be displayed immediately. The image memory 120 may comprise any known data storage medium, for example, a permanent storage medium, removable storage medium, and the like. Additionally, the image memory 120 may be a non-transitory storage medium.

In operation, an ultrasound system may acquire data, for example, volumetric data sets by various techniques (for example, 3D scanning, real-time 3D imaging, volume scanning, 2D scanning with probes having positioning sensors, freehand scanning using a voxel correlation technique, scanning using 2D or matrix array probes, and the like). Ultrasound images of the system 100 may be generated from the acquired data (at the system controller 116) and displayed to the operator or user on the display device 118.

The system controller 116 is operably connected to a user interface 122 that enables an operator to control at least some of the operations of the system 100. The user interface 122 may include hardware, firmware, software, or a combination thereof that enables a user (e.g., an operator) to directly or indirectly control operation of the system 100 and the various components thereof. As shown, the user interface 122 includes a display device 118 having a display area 117. In some embodiments, the user interface 122 may also include one or more input devices 115, such as a physical keyboard, mouse, and/or touchpad. In an exemplary embodiment, the display device 118 is a touch-sensitive display (e.g., touchscreen) that can detect a presence of a touch from the operator on the display area 117 and can also identify a location of the touch in the display area 117. The touch may be applied by, for example, at least one of an individual's hand, glove, stylus, or the like. As such, the touch-sensitive display may also be characterized as an input device that is configured to receive inputs from the operator. The display device 118 also communicates information from the system controller 116 to the operator by displaying the information to the operator. The display device 118 and/or the user interface 122 may also communicate audibly. The display device 118 is configured to present information to the operator during the imaging session. The information presented may include ultrasound images, graphical elements, user-selectable elements, and other information (e.g., administrative information, personal information of the patient, and the like).

As described above, an ultrasound probe includes one or more active components for generating an ultrasonic signal. An example of an active component, or piezoelectric element 202 of an ultrasound probe is shown in a schematic diagram of an acoustic stack 200 in FIG. 2. The piezoelectric element 202 has a central axis 204. A set of reference axes 210 are provided indicating a y-axis, an x-axis, and z-axis. The piezoelectric element 202 is shown in FIG. 2 with the central axis 204 parallel with the z-axis. However, other orientations of the piezoelectric element 202 with respect to the set of reference axes 210 are possible.

While a single piezoelectric element is shown in FIG. 2, the ultrasound probe may include a plurality of piezoelectric elements arranged in an array and individually coupled to an electrical energy source by wires. Each of the plurality of piezoelectric elements may be electrically insulated from adjacent piezoelectric elements but may all be coupled to common layers positioned above and below the piezoelectric element, with respect to the z-axis. The plurality of piezoelectric elements and accompanying layers may be enclosed by an outer housing of the ultrasound probe. The outer housing may be a plastic case with a variety of geometries. For example, the outer housing may be a rectangular block, a cylinder, or a shape configured to fit into a user's hand comfortably. As such, components shown in FIG. 2 may be adapted to have geometries and dimensions suitable to fit within the outer housing of the ultrasound probe.

The piezoelectric element 202 may be a block formed of a natural material such as quartz, or a synthetic material, such as lead zirconate titanate, that deforms and vibrates when a voltage is applied by, for example, a transmitter such as the transmitter 102 of FIG. 1. In some examples, the piezoelectric element 20 may be a single crystal with crystallographic axes, such as lithium niobate and PMN-PT (Pb(Mg$_{1/3}$Nb$_{2/3}$)O$_3$—PbTiO$_3$). The vibration of the piezoelectric element 202 generates an ultrasonic signal comprising ultrasonic waves that are transmitted out of the ultrasound probe in a direction indicated by arrows 203. The piezoelectric element 202 may also receive ultrasonic waves, such as ultrasonic waves reflected from a target object, and convert the ultrasonic waves to a voltage, the voltage transmitted to a receiver of the ultrasound imaging system, such as the receiver 108 of FIG. 1, to be processed into an image.

Electrodes 214 may be in direct contact with the piezoelectric element 202 to transmit the voltage via wires 215, the voltage converted from ultrasonic waves. The wires 215 may be connected to a circuit board (not shown) to which a plurality of wires from electrodes of the plurality of piezoelectric elements may be fixed. The circuit board may be coupled to a coaxial cable providing electronic communication between the ultrasound probe and the receiver.

An acoustic matching layer 220 may be arranged above the piezoelectric element 202, with respect to the z-axis, oriented perpendicular to the central axis 204. The acoustic matching layer 220 may be a material positioned between the piezoelectric element 202 and a target object to be imaged. In some examples, the acoustic matching layer 220 may be a layer extending along the x-axis so that the acoustic matching layer 220 is positioned above each of the plurality of the piezoelectric elements of the ultrasound probe.

The material of the acoustic matching layer 220 may be a composite material, such as an epoxy resin or polymer mixture, with a desired acoustic impedance that falls between an acoustic impedance of the piezoelectric element 202 and an acoustic impedance of the target object. In some examples, the acoustic matching layer 220 may include more than one layer to provide a more gradual transition in impedance between the piezoelectric element 202 and the target object. The impedances of the piezoelectric element 202 and the target object may be sufficiently different that ultrasonic waves emitted by the piezoelectric element 202 may be reflected off the target object rather than entering the target object. By arranging the acoustic matching layer 220 in between, the ultrasonic waves may first pass through the acoustic matching layer 220, emerging from the acoustic matching layer 220 in phase, with a reduced likelihood of reflection at the target object. The acoustic matching layer 220 may shorten a pulse length of the ultrasonic signal, thereby increasing an axial resolution of the signal.

A backing 226 may be arranged below the piezoelectric element 202, with respect to the z-axis. In some examples, the backing 226 may be a block of material that extends along the x-axis so that each of the plurality of piezoelectric elements in the ultrasound probe are directly above the backing 226. The backing 226 may be configured to absorb ultrasonic waves directed from the piezoelectric element 202 in a direction opposite of the direction indicated by arrows 203 and attenuate stray ultrasonic waves deflected by the outer housing of the ultrasound probe. A bandwidth of the ultrasonic signal, as well as the axial resolution, may be increased by the backing 226. Acoustic effects of the backing 226 may be dependent upon a material and structure of the backing 226.

Relative thicknesses of each of the acoustic matching layer 220, the piezoelectric element 202, and the backing 226 may vary depending on materials of each of the components and wavelengths of the ultrasonic signals. The piezoelectric element 202 may have a thickness 228 equal to half of a wavelength of the ultrasonic wave that the ultrasound probe is configured to transmit and the acoustic matching layer 220 may have a thickness 230 equal to a quarter of the wavelength of the ultrasonic waves of the ultrasound probe. A thickness 232 of the backing 226 may range from ≤1 mm up to 20 or 30 mm. A thicker backing may provide increased acoustic attenuation may not allow the backing 226 to be thermally integrated into the acoustic stack 200 and inhibit heat conduction through the backing 226. Thus the thickness 232 may be tuned to provide a desirable balance between acoustic attenuation and thermal conductivity.

An acoustic impedance of the backing 226 may be adapted to the acoustic impedance of the piezoelectric element 202 to allow efficient excitation of the ultrasonic waves. When the acoustic impedance of the backing 226 matches the acoustic impedance of the piezoelectric element 202, signal resolution may be increased but energy may be transferred into the backing 226. The energy may be absorbed by the backing 226, reducing efficiency and leading to a darker image. However, when no backing 226 is present, efficiency may be high but image resolution may be low. Therefore, the acoustic impedance of the backing 226 may be adjusted to enable both a desirable degree of both resolution and efficiency.

A high acoustic attenuation coefficient of the backing 226 may be desirable to readily absorb scattered ultrasonic waves within the probe that may otherwise be reflected back to the piezoelectric element 202. Thus the material of the backing 226 may have a density within a target range to impart the backing 226 with suitable impedance and attenuation properties. Furthermore, the backing 226 may be configured to increase a frequency bandwidth of the probe to enhance a signal-to-noise ratio of the probe and decrease a pulse length of the ultrasonic signal without altering a frequency of the signal. The backing 226 may also possess high thermal conductivity to dissipate heat produced by the piezoelectric element 202 during active signal generation and conduct the heat away from the ultrasound probe to heat sinks. In some examples, mechanical properties such as high tensile strength, high yield strength, etc., may be demanded of the backing 226 to allow positioning of the backing 226 adjacent to rigid components such as the electrodes 214 without deformation of the backing 226.

Conventional techniques for fabricating the material of the backing 226 may include casting or pressing a composite material. In some examples, the composite material may be a mixture of metal (e.g., tungsten or tin powder) or ceramic (e.g., aluminum nitride) with a polymer or epoxy. Alternatively, in other examples, the composite material may be highly absorbing constituents such as powders of elastomeric materials. However, the polymer may have a relatively low heat tolerance and may not be used in high temperature applications. In other examples, the composite material may be formed from a graphite foam or porous copper impregnated with epoxy, the graphite foam or porous copper providing high thermal conductivity away from the piezoelectric element 202. Both the graphite foam and porous copper may impose high costs on the probe, however, while the conventional casting or pressing processes are also costly and inefficient due to a demand for secondary machining during manufacturing. In addition, properties, both acoustic and thermal, of the composite materials described above may not be tuned during fabrication to accommodate variations in ultrasonic signal intensity, frequency, scattering, etc., arising between different ultrasound probes.

Attempts to address the cost of conventional fabrication methods include adapting additive manufacturing, such as 3D printing, to form the composite material for the backing 226. A data set for additively manufacturing a supporting structure for the backing material that is impregnated with an acoustic attenuating component may be prohibitively large. For example, the data set may be stored in a memory of a system controller of a 3D printer and may occupy a large portion of the memory. Due to a size of the data set, the retrieval and execution of instructions by the system controller may be inefficiently slow. In some cases, the size of the data set may even cause the system controller to freeze and request rebooting.

Thus, according to embodiments disclosed herein, the issues described above may be addressed by methods and systems for forming the backing by additively manufacturing at least one component of the backing in stacked, tessellated layers. As used herein, a tessellation pattern may describe a tiled geometric shape that is arrangement in a repetitive manner to cover a plane without presence of interstices between the repeating shape or overlap of the shape. The data set for additive manufacturing of the backing may include two sets of instructions: a first set commanding printing of a first tessellated layer and a second set commanding printing of a second tessellated layer that may be similar to or differ from the first set and configured to align with the first layer in a manner that affects acoustic properties of the backing. The system controller may alternate between printing the first layer and second layer repeatedly until a target thickness of the backing is attained. In this way, the data set is reduced to two small sets of instructions that may retrieved and executed repeatedly rather than one large set of instructions that may be retrieved and executed once, allowing the system controller to efficiently access and implement the stored information.

The formation of the backing material in layers may also allow the backing material to be readily varied, with regards to geometry and alignment of stacked layers. For example, the tessellated pattern may be based on a specific void shape, such as a circle, square, triangle, or hexagon. As another example, the tessellated pattern may be random geometries, configured with minimal constraints, e.g., a target size and material defining the voids, to form an open cell structure. A stack-up from such a configuration may be semi-random, with alternating layers of a first and a second layer, as shown in FIGS. 3A-8B, with a same pattern of voids present in each layer. Thus the randomness is constrained to each layer. As the layers of the backing material are stacked, the material forms an open cell microstructure. A geometry of each cell of the open cell microstructure may be shaped by the alignment of the layers. If the layers are exactly aligned, each cell may have a shape based on the tessellated pattern. As an example, tessellated layers of a repeating pattern of circular voids may be stacked so that voids of each layer are aligned with adjacent layers. The cells, formed of stacked voids, may also have a uniformly circular cross-section, the cross-section perpendicular to a direction of stacking. However, if the second layer is offset from the first layer, the cells may have a non-uniform cross-sectional shape with discontinuous walls. In other examples, the staggering of layers may result in irregular, variable cell geometries. Examples of various patterns and stacking schemes and effects on acoustic properties are described further below with reference to FIGS. 3A-8C.

Figure 3A:
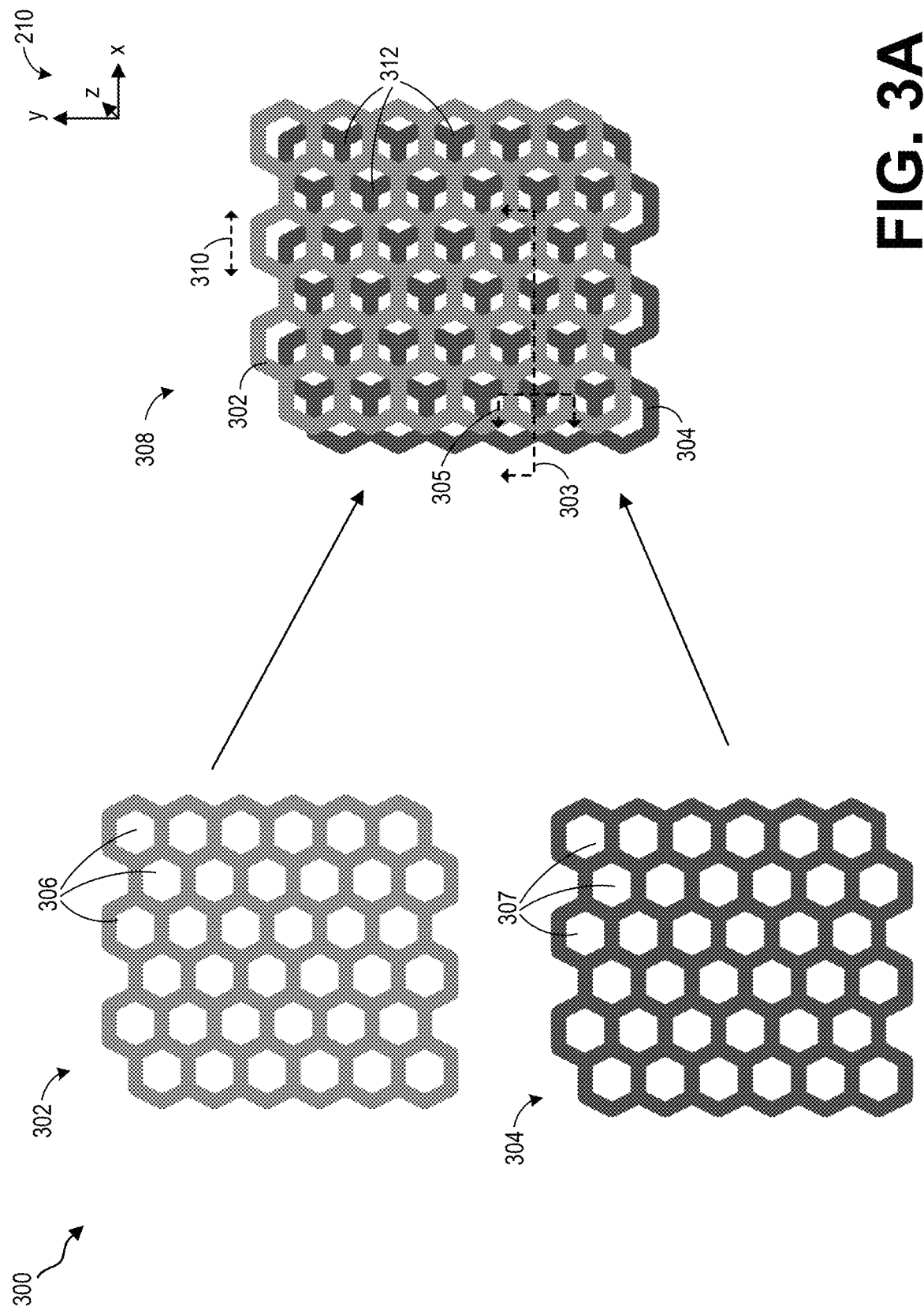
FIG. 3A shows an example of a first tessellation pattern for a backing material of an ultrasound probe.

An example of a first tessellation pattern 300 is shown in FIG. 3A from a top-down view, e.g., viewed along the z-axis. The first tessellation pattern 300 is incorporated into both a first layer 302 and a second layer 304. The first layer 302 and the second layer 304 are identical, where the first layer 302 is formed of a sheet of material patterned with a first set of voids 306 and the second layer 304 is formed of a sheet of material patterned with a second set of voids 307. Each hexagonal void of the first set of voids 306 may be spaced apart from adjacent voids by the material of the first layer 302. Likewise, each hexagonal void of the second set of voids 307 of the second layer 304 may be spaced apart from adjacent voids by a material of the second layer 304. Each of the first layer 302 and the second layer 304 may be 200-400 μm thick. The first layer 302 and the second layer 304 may be stacked to form a first meta-structure 308, with the second layer 304 under the first layer 302, with respect to the z-axis. The first meta-structure 308 may be a framework or scaffold used to form an open-cell structure in a backing of an ultrasound probe.

The second layer 304 may be offset from the first layer 302 by half of a width 310 of a void from the first set of voids 306 or the second set of voids 307. In one example, the width 310 of the void may be 400 µm or less. While the first meta-structure 308 is shown as a stack of one each of the first layer 302 and second layer 304 for simplicity, the first meta-structure 308 may include many sheets of the first layer 302 and the second layer 304, alternating so that each sheet of the first layer 302 is sandwiched between a sheet of the second layer 304 below and another sheet of the second layer 304 above and similarly, each sheet of the second layer 304 is sandwiched between a sheet of the first layer 302 below and another sheet of the first layer 302 above (other than top and bottom layers of the meta-structure 308). The first layer 302 and the second layer 304 may be repeatedly stacked until the first meta-structure 308 achieves a desired thickness, as measured along the z-axis, such as between ≤1 mm up to 20 or 30 mm.

By stacking the first layer 302 and the second layer 304 in an offset, staggered manner to form the first meta-structure 308, the first meta-structure 308 may have a structure defined by the materials of the layer 302 and the second layer 304, forming a scaffold in which cells 312 may be disposed. The cells 312 may be openings that extend linearly through the thickness of the meta-structure, each cell of the cells 312 defined by the material surrounding the first set of voids 306 and the material surrounding the second set of voids 307 of the first layer 302 and the second layer 304, respectively. A volume of the cells 312 of the first meta-structure 308 may be reduced compared to a volume of the cells 312 when the first layer 302 and the second layer 304 are aligned. When the first meta-structure 308 has aligned layers, each pore may have a uniform diameter equal to the width 310 of the hexagonal voids 306 through the thickness of the meta-structure. In contrast, when the first layer 302 and the second layer 304 are not aligned, as shown in FIG. 3A, the cells 312 may have a narrower diameter due to the staggered alignment of the first layer 302 and the second layer 304. A configuration of the meta-structure 308 is shown in greater detail in a first cross-section 303 depicted in FIG. 3B and a second cross-section 305 depicted in FIG. 3C.

The first cross-section 303, taken along the z-x plane as indicated in FIG. 3A, shows the first meta-structure 308 as a stack of layers of the first tessellation pattern 300 including the first layer 302, the second layer 304, a third layer 318, a fourth layer 320, a fifth layer 322, and a sixth layer 324. The first layer 302, the third layer 318, and the fifth layer 322 may be aligned with one another along the z-axis. The second layer 304, the fourth layer 320, and the sixth layer 324 may aligned with one another, also along the z-axis. Voids in the layers are depicted with cross-hatching. A first cell 326 and a second cell 328, which may be examples of the cells 312 of the first meta-structure 308 shown in FIG. 3A, are indicated by dashed lines and dotted shading, extending linearly through a thickness 316 of the first meta-structure 308.

The first cell 326 and the second cell 328 extend through the entire thickness 316 of the meta-structure 308. As result of the offset alignment between the layers of the first meta-structure, the first cell 326 and the second cell 328 include portions of voids in each layer. For example, a first void 306a of the first set of voids 306 of the first layer 302 is aligned above and to the left of a first void 307a of the second set of voids 307 of the second layer 304. A first void 330 of the third layer 318 is aligned with the first void 306a of the first layer 302. A portion of the first void 306a of the first layer 302 may be included in the first cell 326 as well as a portion of the first void 307a of the second layer 304 and a portion of the first void 330 of the third layer 318. As the first cell 326 continues down through the first meta-structure 308, the first cell 326 is formed from a portion of a void from each layer, the portion from each void stacked on top of one another along the z-axis.

A width 314 of the first cell 326 (and the second cell 328) may be reduced in comparison to when the layers of the first meta-structure 308 are all aligned. As described above, when the layers of the first meta-structure 308 are aligned, the width 314 of the cells 312 may be equivalent to the width 310 of the hexagonal voids. However, staggering the alignment of the layers of the first meta-structure 308 decreases the width 314 of the cells 312 of the first meta-structure 308.

The offset of the layers of the meta-structure 308 may also alter a fluid communication between voids of one layer and voids of adjacent layers due to an overlapping between voids of different layers. When the layers are aligned, the voids of the layers are aligned across the entire width of the voids and directly coupled to an entirety of a void a in layer above and an entirety of a void in a layer below. In the staggered alignment of FIGS. 3A-3C, however, the voids are offset along the x-axis as shown in FIG. 3B and also along the y-axis as shown in the second cross-section 305 of FIG. 3C. The voids may overlap, along the z-axis, across portions of the widths of the voids. As a result, the first void 306a of the first layer 302 may be fluidly coupled to the first void 307a of the second layer 304 through the portions of both voids included in the first cell 326. The first void 306a may also be fluidly coupled to two more voids in the second layer 304, one of the two voids arranged in front of the first void 307a and offset to the left, and another of the two voids arranged behind the first void 307a and also offset to the left. Similarly, the first void 307a of the second layer 304 may be fluidly coupled to the first void 306a of the first layer 302 as well as two more voids of the first layer 302. One of the two voids may be in front of the first void 306a and offset to the right and the other of the two voids may be behind the first void 306a and also offset to the right.

The first void 307a of the second layer 304 is also fluidly coupled to the first void 330 of the third layer 318 through the portions of both voids included in the first cell 326. The first void 307a of the second layer 304 is additionally fluidly coupled to two more voids in the third layer 318. One of the two voids may be in front of the first void 330 and offset to the right and the other of the two voids may be behind the first void 330 and also offset to the right. Thus, each void in a layer of the meta-structure 308 may be fluidly coupled to three voids in a layer above and three voids in a layer below with the exception of top and bottom layers of the first meta-structure 308.

The first meta-structure 308 may be a meta-structure that is additively manufactured as the framework for the backing material of the ultrasound probe, such as the ultrasound probe 106 of FIG. 1. The meta-structure of the backing material may be a more rigid component of the backing material, providing stability and thermal conductivity. The meta-structure may be formed from a ceramic or an insulated metal (e.g., to decrease a likelihood of electrical shorting in the probe).

In addition to offering structural support and efficient heat transfer, the meta-structure of the backing material may also be an acoustic diffusor. The meta-structure may reduce generation of echoes and reflections within the ultrasound probe by radiating the ultrasonic waves in many directions, thereby allowing a more diffusive acoustic space within the backing material, thus increasing average ultrasonic wave path length and energy absorption.

Figure 3C:
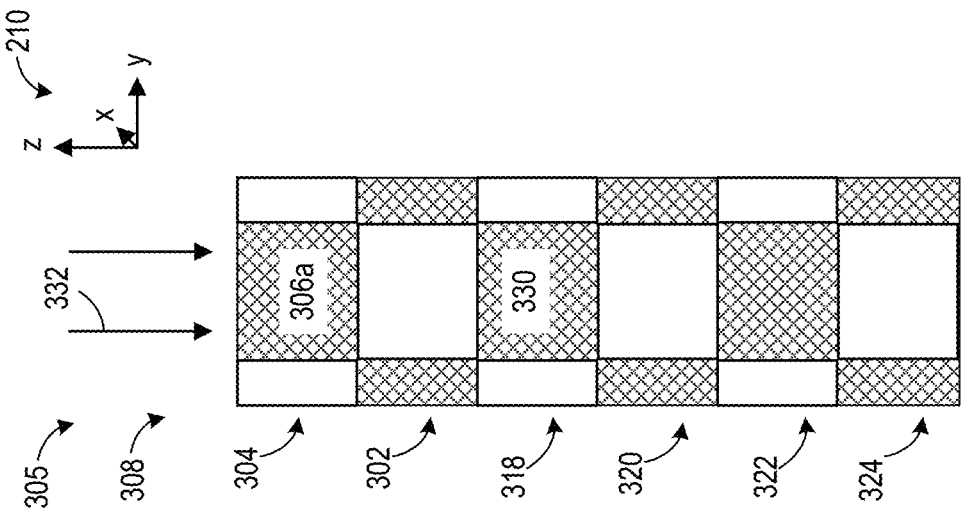
FIG. 3C shows a second cross-section of the first tessellation pattern.
Figure 3B:
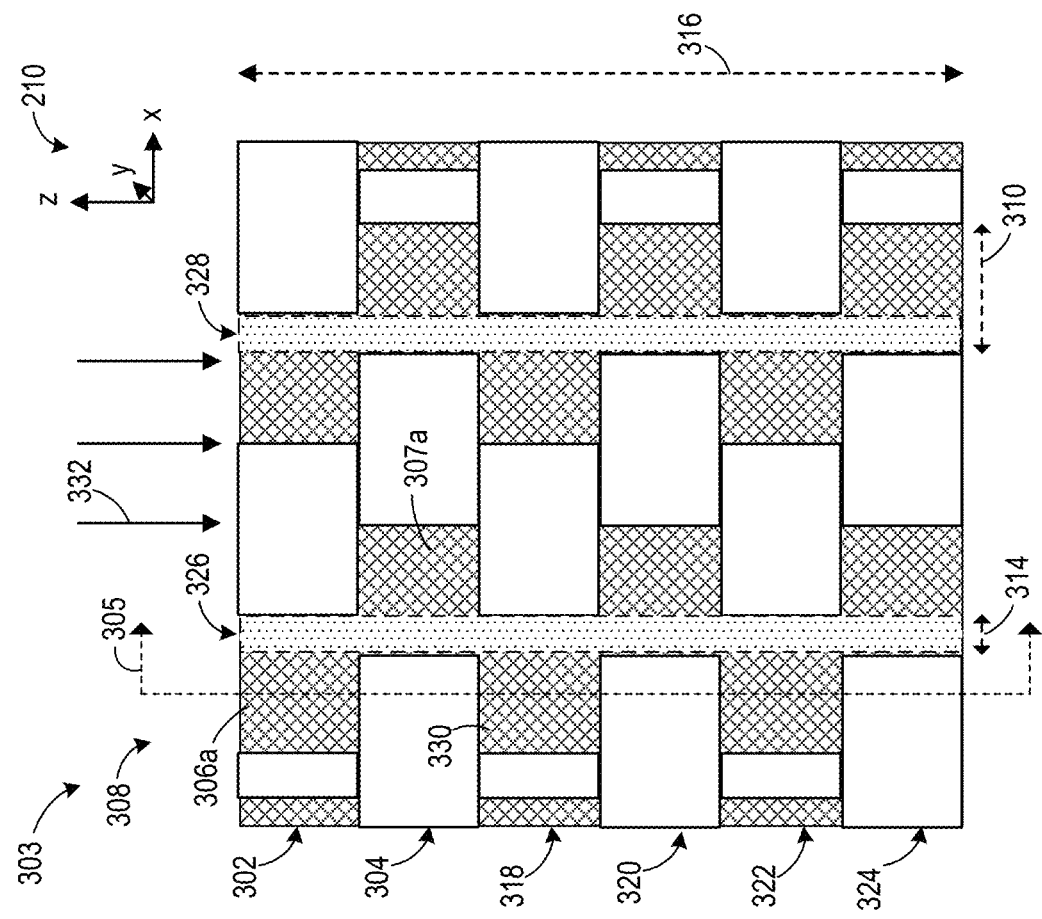
FIG. 3B shows a first cross-section of the first tessellation pattern

Thus, when the layers of the first meta-structure 308 are staggered as shown in FIGS. 3A-3C, a likelihood of interaction between acoustic waves entering the first meta-structure 308, as indicated by arrows 332 in FIGS. 3B-3C, and the material of the first meta-structure 308 is increased compared to when the layers are aligned. The incoming acoustic waves may strike either the voids in a top layer of the backing material or the material of the meta-structure. When the layers of the meta-structure are offset, waves entering the backing material through the voids are more likely to continue travelling to an underlying segment of the material of the meta-structure than when the layers are aligned. Similarly, when the waves initially strike the material of the meta-structure, the waves are more likely to continue travelling into a void of the meta-structure. Thus a probability that incoming acoustic waves interact with both the diffusing material of the meta-structure and an attenuating material filling the voids of the meta-structure is enhanced.

Cells and voids of the meta-structure, formed from additively manufactured sheets of a tessellated pattern, such as the first tessellation pattern 300 of FIG. 3A, may be filled with a softer component with acoustic attenuating properties. The softer component may be a polymer such as epoxy or impregnated polyurethane that is added to the meta-structure after the meta-structure is printed. Alternatively, the backing material may be additively manufactured with the softer component incorporated into the meta-structure during printing of the meta-structure.

The softer component may allow the backing material to attenuate ultrasonic waves within the probe that are propagated within an interior of the probe. Acoustic attenuation properties of the softer component and the meta-structure may result in scattering and absorption of ultrasonic waves in the interior of the probe emitted from the piezoelectric crystal. By efficiently attenuating the ultrasonic waves, a likelihood of wave scattering within probe interior is reduced, which may otherwise interfere with an ultrasonic signal beam directed at a target object. Without a high degree of attenuation in the backing material, the signal beam may have poor axial resolution.

An effectiveness of the backing material towards impeding, attenuating, and diffusing a wide frequency bandwidth of ultrasonic waves may be moderated by adjusting geometric parameters of the meta-structure. Varying the tessellation pattern, line width, and layer thickness of the material defining the voids allows tuning of the backing material to enhance specific effects of the backing material. As described above, the diffusing effect of the backing material, and thereby the acoustic attenuation, may be increased by offsetting the first layer 302 and the second layer 304 of the first meta-structure 308. In addition to the alignment of the layers of the meta-structure of the backing material, acoustic properties of the backing material may be further modified by varying a line width of the tessellation pattern of the meta-structure, as shown in an example of a second tessellation pattern 400 in FIG. 4A.

The second tessellation pattern 400 has a first layer 402 and a second layer 404. The second layer 404 of the second tessellation pattern 400 may be similar to the first layer 302 and the second layer 304 of the first tessellation pattern 300 of FIG. 3A with a similar line width 410 that is wider than a line width 408 of the first layer 402. The first layer 402 may be a layer of material with a first set of hexagonal voids 406 and the second layer 404 may be a layer of material with a second set of hexagonal voids 412. The material of the first layer 402 may be the same as the material of the second layer 404 and a diameter 416 of the first set of voids 406 may be similar or different from a diameter 422 of the second set of voids.

The first layer 402 may be stacked over the second layer 404 to form a second meta-structure 414. The second layer 404 may be offset from the first layer 402 by half of the diameter 422 of the first set of voids 406 of by half of the diameter 422 of the second set of voids 412 in the second meta-structure 414 along one edge of the second meta-structure 414, e.g., the left edge. In some examples, the offset of the first layer 402 from the second layer 404 may not remain consistently as half of the diameter across the second meta-structure 414 due to the difference in void diameter and line width between the first layer 402 and the second layer 404.

The stacking of the first layer 402 over the second layer 404 may be repeated until a desired thickness of the second meta-structure is attained. As shown in a first cross-section 403 and a second cross-section 405 in FIGS. 4B and 4C, respectively, the second meta-structure 414 may comprise six layers in total, for example. The second meta-structure 414 may have cells 418 extending through an entire thickness of the second meta-structure 414. A volume and geometry of each of the cells 418 may be defined by the stacking of the layers of the second meta-structure 414 and is depicted in greater detail in the first cross-section 403 and the second cross-section 405.

The second meta-structure 414 shown in the first cross-section 403 and second cross-section 405 in FIGS. 4B-4C is a stack with the first layer 402, the second layer 404, a third layer 430, a fourth layer 432, a fifth layer 434, and a sixth layer 436. The first layer 402, the third layer 430, and fifth layer 434 may be identical and aligned with one another while the second layer 404, the fourth layer 432, and the sixth layer 436 may be identical and aligned with one another.

A first cell 438 and a second cell 440 of the cells 418 may extend linearly through the thickness 442 of the second meta-structure 414. A width 444 of the first cell 438 may be bound by edges of the material of the first layer 402, third layer 430, and fifth layer 434 on the right and by edges of the material of the second layer 404, fourth layer 432, and sixth layer 436 on the left. The width 444 of the first cell 438 may be similar to a width 446 of the second cell 440 but may be different in other examples, depending on the different in diameters between the first set of voids 406 of the first layer 402 and the second set of voids 412 of the second layer 404. Both the widths 444 and 446 of the first cell 438 and the second cell 440 may be narrower than the widths of the voids.

Figure 4A:
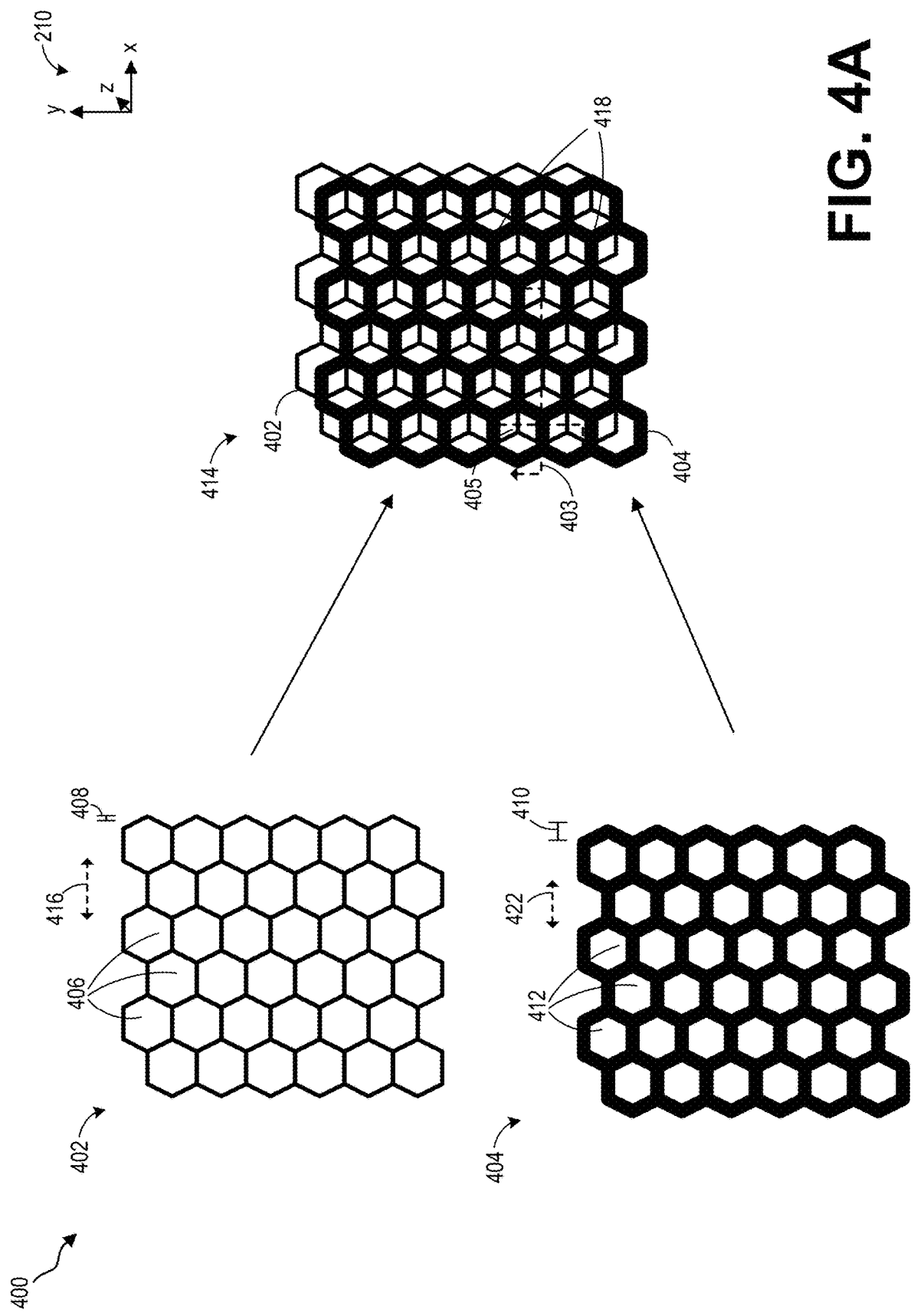
FIG. 4A shows an example of a second tessellation pattern for a backing material of an ultrasound probe.

The alignment of voids in the second meta-structure 414 as shown in FIGS. 4A-4B are similar to the alignment of voids in the first meta-structure 308, as shown in FIGS. 3A-3B. Each void of each layer of the second meta-structure 414 overlaps with a portion of a void in an adjacent layer and the overlapping portion is included in a cell of the second meta-structure 414. For example, a portion of a first void 406a of the first set of voids 406 of the first layer 402 overlaps with a portion of a first void 412a of the second set of voids 412 of the second layer 404 arranged below and to the right of the first void 406a of the first layer 402. Another portion of the first void 412a of the second layer 404 also overlaps with a portion of the first void 448 of the third layer 430, arranged below and to the left of the first void 412a of the second layer 404. The voids of each layer of the second meta-structure 414 are similarly staggered along the x-axis, as indicated by the second cross-section 405 of FIG. 4C, taken along a plane perpendicular to the first cross-section 403 of FIG. 4B.

Each void of each layer of the second meta-structure may be fluidly coupled to three voids in a layer above and three voids in a layer below, as described above for the first meta-structure 308 of FIGS. 3A-3C. When, for example, the line width 410 of the second layer 404 of the second tessellation pattern 400 is equal to a line width of the first layer 302 and second layer 304 of the first tessellation pattern of FIGS. 3A-3C, a volume fraction of the cells 418 of the second meta-structure 414 may differ from a cellular volume fraction of the first meta-structure 308 due to the narrower line width 408 of the first layer 402. The cellular volume fraction of the second meta-structure 414 may be greater than the cellular volume fraction of the first meta-structure 308. However, if the first layer 402 of the second meta-structure 414 has a thicker line width than the first layer 402, the cellular volume fraction of the second meta-structure 414 may instead be less than the cellular volume fraction of the first meta-structure 308.

Varying a volume fraction of cells of a meta-structure for an ultrasound probe backing may vary a density of the backing. Modifying the density of the backing material may alter an acoustic impedance of the backing materials. As acoustic impedance is a product of a density of a material and an acoustic velocity of an acoustic signal, increasing the density may increase an acoustic impedance of the meta-structure and decreasing the density may decrease the acoustic impedance. The acoustic impedance of the first meta-structure 308 may thereby be adjusted to match the impedance of a piezoelectric crystal, such as the piezoelectric element 202 of FIG. 2.

The density of the backing material may be controlled by additively manufacturing the meta-structure with a line width of one of two layers of the meta-structure adapted to impart the resulting backing material with a desired degree of acoustic impedance. The line width of one of the layers may be adjusted without adding complexity to a data set used by a 3D printing system to generate the meta-structure. For example, the printing system may use a data set for two layers used to generate the first meta-structure 308 of FIGS. 3A-3C and modify a line width of one of the layers to obtain a target cellular volume fraction of the layer.

The density of the backing material may also be adjusted by varying a thickness of the layers of the meta-structure. For example, both the thickness of the first layer 402 and the thickness of the second layer 404 may be increased to increase a cellular volume fraction of both layers and decrease the density of the backing material. Decreasing the thickness of the first layer 402 and second layer 404 may decrease the cellular volume fraction of both layers and increase the density of the backing material. As another example, the height of one layer may be varied independently of the other layer to similarly modify an acoustic impedance capacity of the backing material.

Acoustic properties of a backing of an ultrasound probe may also be adjusted by varying a geometric shape that is repeated in a layer with a tessellated pattern of voids in a meta-structure of a backing material. In FIGS. 5A-8B, alternative shapes that may serve as a basis for tessellation are shown, depicting patterns based on squares, triangles, and circles, respectively. In an example of a third tessellated pattern 500 in FIG. 5A, a third meta-structure 506 may be formed from stacking a first layer 502 over a second layer 504 of the third tessellated pattern 500.

The first layer 502 and the second layer 504 of the third meta-structure 506 may be identical, formed from a repeating pattern of a first set of voids 508 in the first layer 502 and a second set of voids 514 in the second layer 504 that are square along the y-x plane. The first layer 502 may be stacked over the second layer 504 so that the layers are offset by half of a width 510 of the first set of voids 508, which is also half of a width of the second set of voids 514. Resulting cells 512 of the third meta-structure 506 may have a regular and uniform alignment through a thickness of the third meta-structure 506 as shown in a first cross-section 503 and a second cross-section 505 in FIGS. 5B and 5C, respectively.

The first cross-section 503 and the second cross-section 505 depict the third meta-structure 506 as a stack of layers including the first layer 502, the second layer 504, a third layer 516, a fourth layer 518, a fifth layer 520, and a sixth layer 522. The first layer 502, third layer 516, and fifth layer 520 are aligned along the z-axis and the second layer 504, fourth layer 518, and sixth layer 522 are also aligned along the z-axis. In the first cross-section 503, taken along the z-x plane and sliced along a section of material of the second layer 504, voids of the first layer 502, third layer 516 and fourth layer 518 are uniform and evenly spaced apart along the x-axis by a material of the first layer 502, third layer 516, and fourth layer 518 as well as by the materials of the layers in between along the z-axis.

Figure 5A:
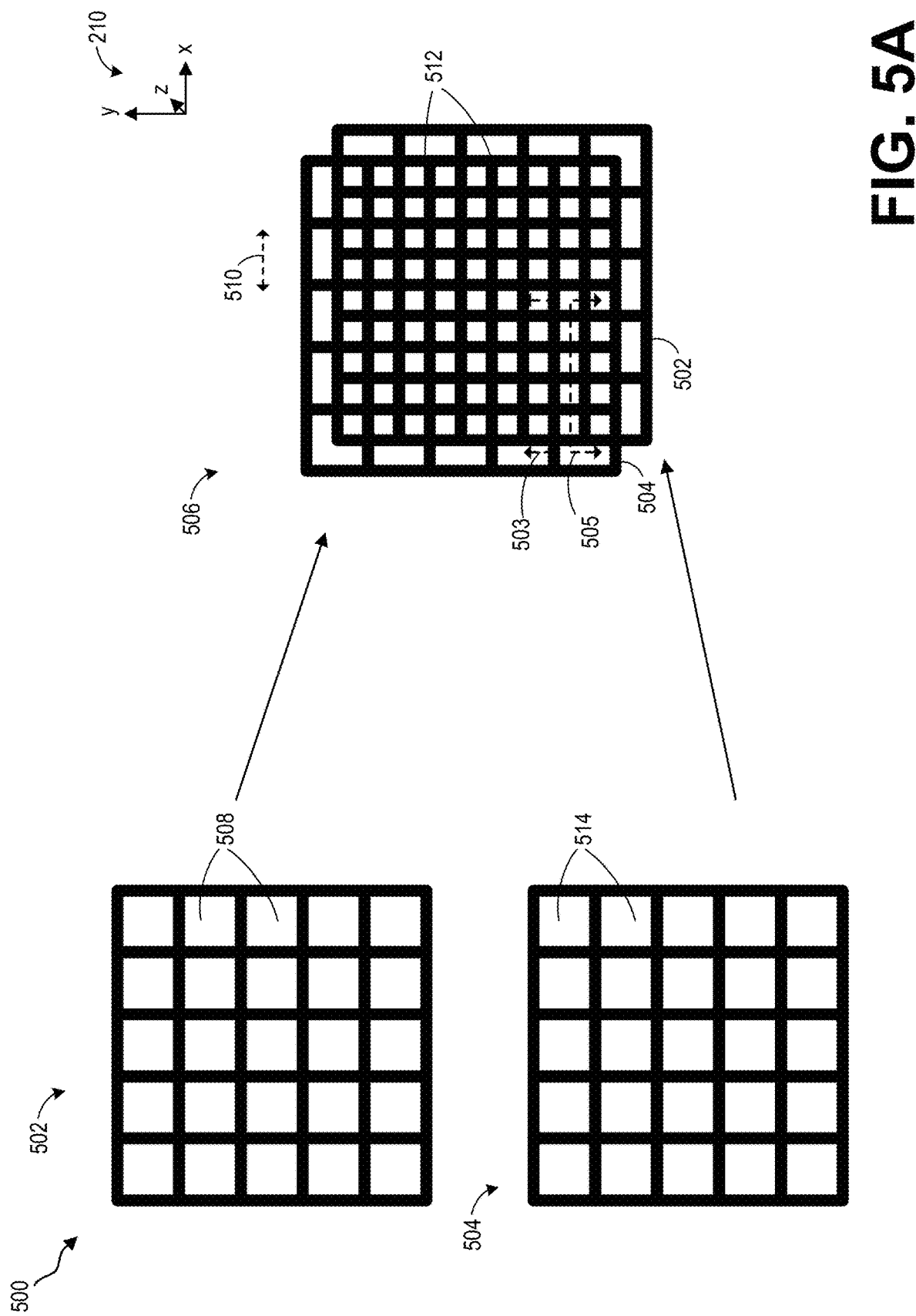
FIG. 5A shows an example of a third tessellation pattern for a backing material of an ultrasound probe.
Figure 5C:
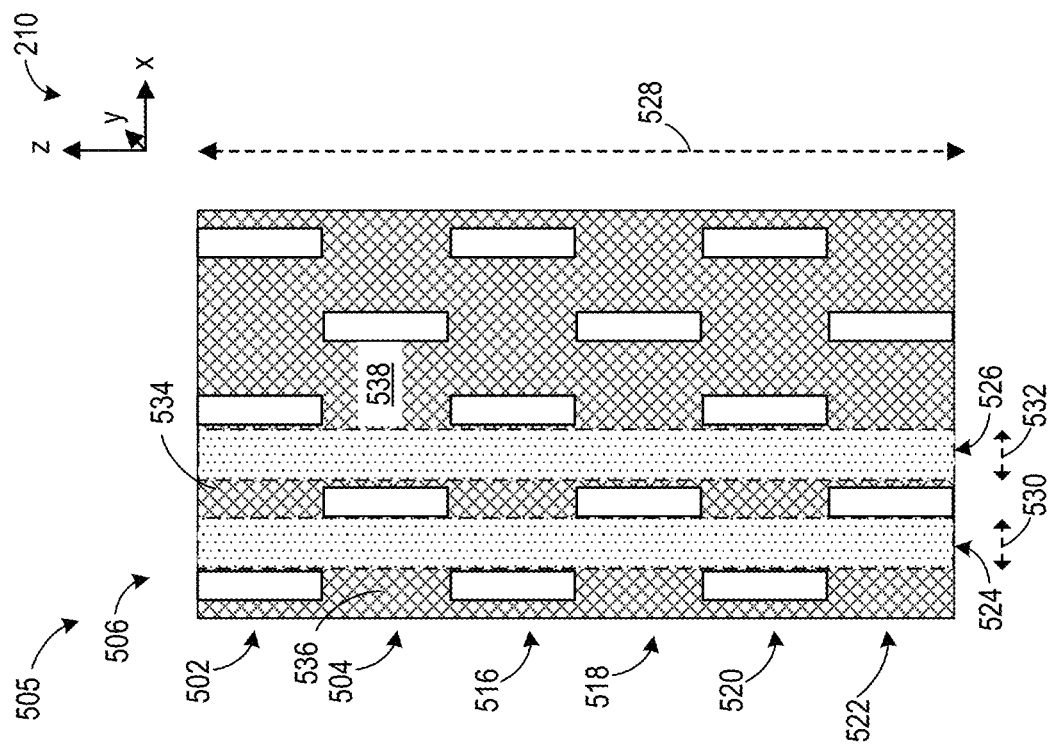
FIG. 5C shows a second cross-section of the third tessellation pattern.
Figure 5B:
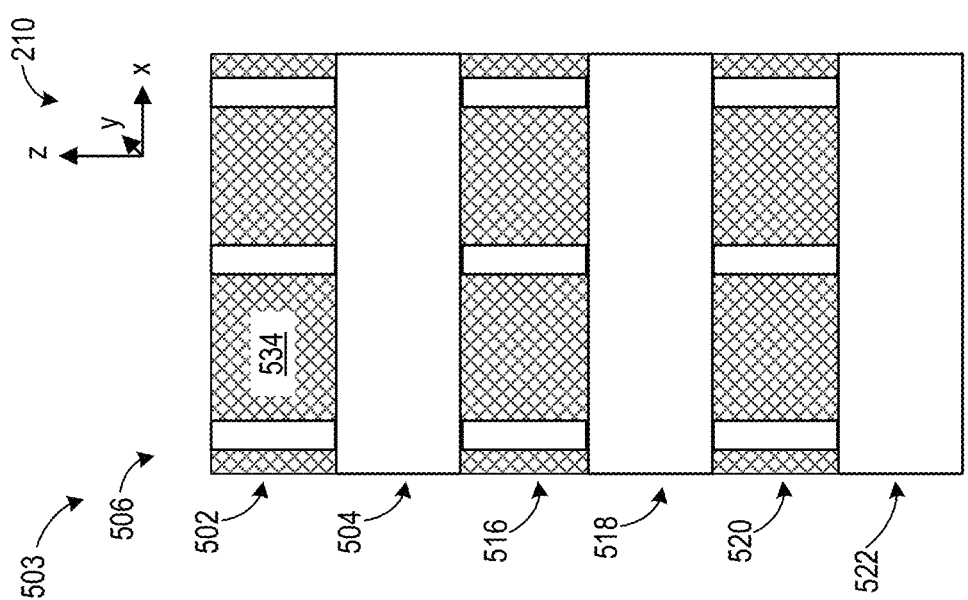
FIG. 5B shows a first cross-section of the third tessellation pattern.

In the second cross-section 505, taken along a the same plane as the first cross-section 503 but slicing through both the first set of voids 508 of the first layer and the second set of voids 514 of the second layer 504, a first cell 524 and a second cell 526 of the cells 512 of the third meta-structure 506 may extend linearly through a thickness 528 of the third meta-structure 506, as shown in FIG. 5C. A width 530 of the first cell 524 may be equal to a width 532 of the second cell 526. All cells 512 of the third meta-structure 506 may have similar dimensions and geometries as the first cell 524 and second cell 526.

A first void 534 of the first set of voids 508 of the first layer 502 may overlap, along the z-axis, with a portion of a first void 536 of the second set of voids 514 of the second layer 504 as well as a portion of a second void 538 of the second set of voids 514 of the second layer 504. The overlapping portions between the first void 536 of the first layer 502 and the first void 536 of the second layer 504 may be included in the first cell 524 and the overlapping portions between the first void 536 of the first layer 502 and the second void 538 of the second layer 504 may be included in the second cell 526. The first void 534 of the first layer 502 may additionally overlap with a void in the second layer 504, in front of and overlapping with both the first void 536 and the second void 538 of the second layer 504, as well as overlapping with a void in the second layer 504, behind and overlapping with both the first void 536 and the second void 538 of the second layer 504. Each void of the third meta-structure 506 is thus fluidly coupled to four voids in a layer above and four voids in a layer below.

While the third tessellation pattern 500 may provide a simple pattern resulting in uniform cells 512 that may be efficiently manufactured with high reproducibility, the third meta-structure 506 may reflect ultrasonic waves predominantly in two directions compared to reflection along three directions in the hexagon-based first meta-structure 308 of FIGS. 3A-3C and second meta-structure 414 of FIGS.

4A-4C. As such, the third meta-structure 506 may provide a lesser degree of acoustic diffusion than the first tessellation pattern 300 and second tessellation pattern 400. In addition to the hexagon-based pattern, a tessellated pattern derived from triangular voids may also reflect ultrasonic waves in three directions.

Figure 6A:
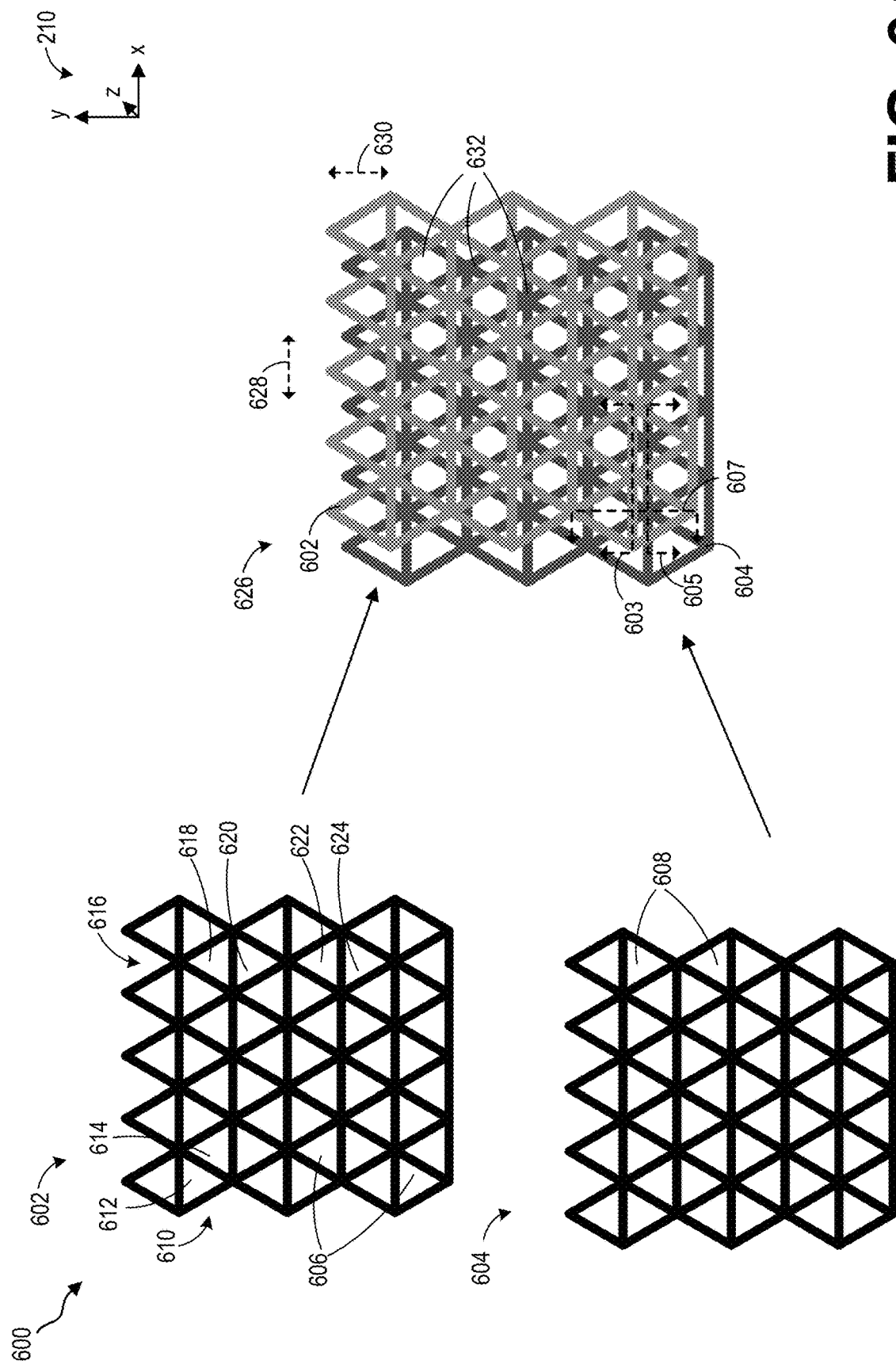
FIG. 6A shows an example of a fourth tessellation pattern for a backing material of an ultrasound probe.

An example of a fourth tessellation pattern 600 is illustrated in FIG. 6A. The fourth tessellation pattern 600 has a first layer 602 and a second layer 604 that are identical. The first layer 602 has a first set of voids 606 and the second layer 604 has a second set of voids 608, both sets of voids depicted as equilateral triangles. In other examples, however, the voids may not be equilateral triangles, having sides that are of a different length than a base of each of the triangles.

The fourth tessellation pattern 600 may be formed from triangles alternating between a first orientation and a second orientation. For example, in a first row 610 of the first layer 602 along the x-axis, a first void 612 of the first set of voids 606 may be in a first orientation with the base at a top, with respect to the y-axis, of the first void 612 and a point at a bottom of the first void 612. A second void 614 is immediately adjacent to and to the right of the first void 612. The second void 614 is flipped upside down relative to the first void 612 with the point of the triangle at a top of the second void 614, with respect to the y-axis, and the base of the triangle at a bottom of the second void 614. By orienting the second void 614 upside down relative to the first void 612, the second void 614 may occupy spaces in between each void of the first set of voids 606 arranged in the first orientation along a row of the first layer 602.

The first set of voids 606 may also alternate between the first orientation and the second orientation in a column 616 along the y-axis. A third void 618 of the first set of voids 606 may be in the first orientation. A fourth void 620 directly adjacent to and below (with respect to the y-axis) the third void 618 is arranged in the second orientation. Together, the third void 618 and the fourth void 620 may form a first diamond. Below the first diamond, along the y-axis, may be a second diamond, formed from a fifth void 622 and a sixth void 624 of the first set of voids 606, arranged in the first orientation and second orientation, respectively.

In other examples, the first set of voids 606 of the first layer 602 and/or the second set of voids 608 of the second layer 604 may be rotated by a number of degrees. For example, the first set of voids 606 may be rotated clockwise by 30 degrees while the second set of voids 608 is maintained in the alignment shown in FIG. 6A. As another example, the first set of voids 606 may be rotated 30 degrees clockwise and the second set of voids 608 rotated 30 degrees counterclockwise. By independently rotating voids of the layers of a meta-structure formed from layers of the fourth tessellation pattern 600, acoustic waves may be reflected through more angles and increased diffusivity of a backing material incorporating the fourth tessellation pattern 600 may lead to broader bandwidth behavior.

The first layer 602 may be stacked on top, with respect to the z-axis, of the second layer 604 to form a fourth meta-structure 626. A thickness, measured along the z-axis, of the fourth meta-structure 626 may include multiple layers aligned with the first layer 602 and multiple layers aligned with the second layer 604 in an alternating configuration. The first layer 602 may be positioned over the second layer 604 so that the first set of voids 606 of the first layer 602 are not aligned with the second set of voids 608 of the second layer 604. In FIG. 6A, the second layer 604 is shown offset from the first layer 602 by half of a width 628 of the triangle base of the first set of voids 606 along the x-axis and by a portion of a height 630 of the voids 606, the height 630 perpendicular to the width 628, along the y-axis. The portion of the height 630 by which the second layer 604 is offset from the first layer 602 may be a fraction of the height 630 that is less than half of the height 630, such as a third or a quarter.

Figure 6D:
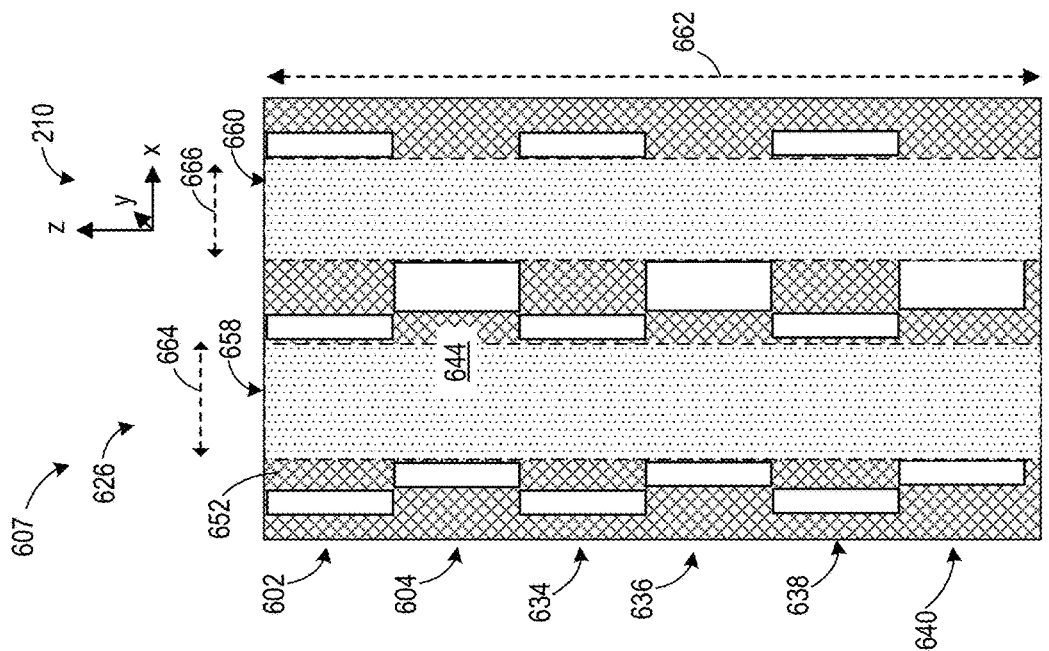
FIG. 6D shows a third cross-section of the fourth tessellation pattern.
Figure 6C:
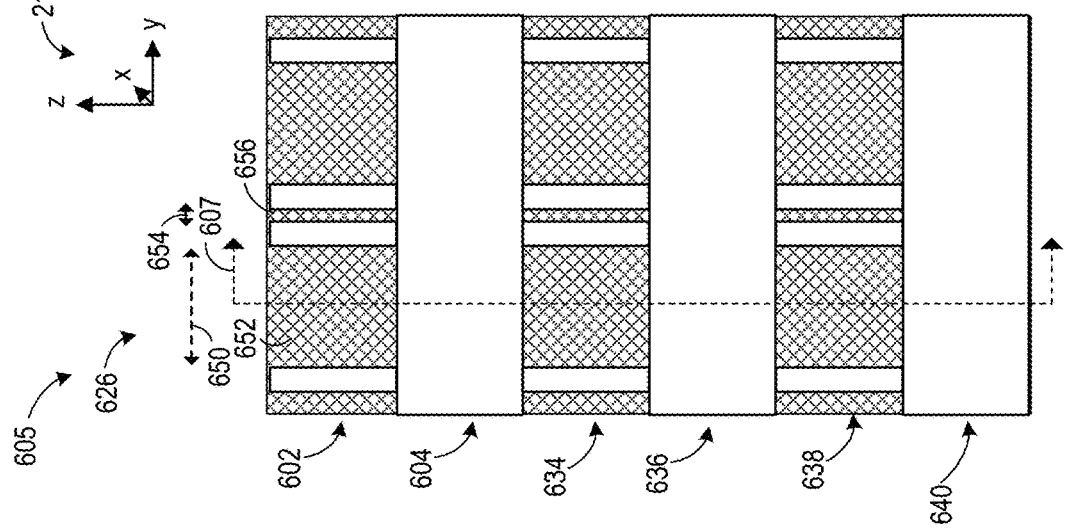
FIG. 6C shows a second cross-section of the fourth tessellation pattern.
Figure 6B:
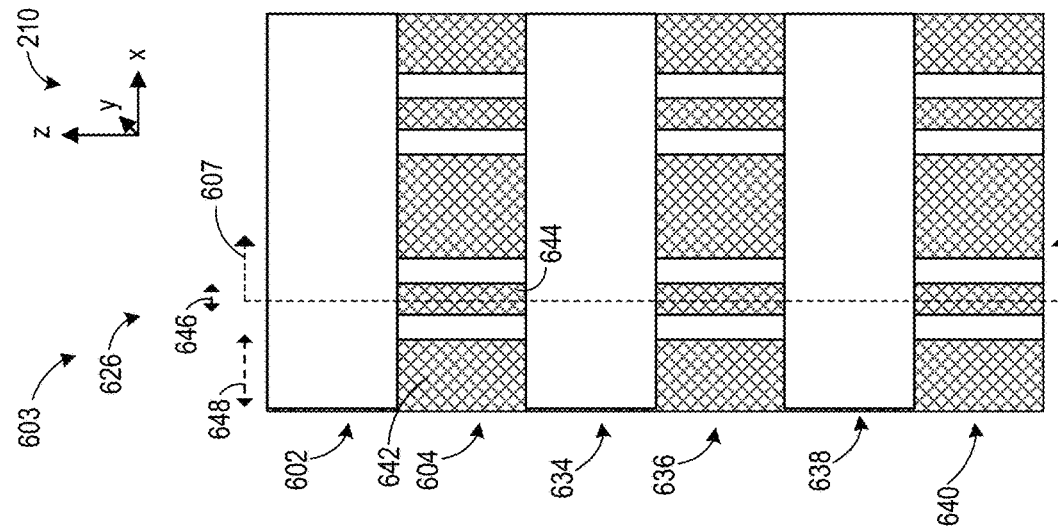
FIG. 6B shows a first cross-section of the fourth tessellation pattern.

The misalignment of the first layer 602 and second layer 604 may result in formation of cells 632 of the fourth meta-structure 626 with irregular shapes and volumes, as shown in a first cross-section 603 in FIG. 6B, a second cross-section 605 in FIG. 6C and a third cross-section 607 in FIG. 6C. The fourth meta-structure 626 is shown in FIGS. 6B-6D as a stack of layers including the first layer 602, the second layer 604, a third layer 634, a fourth layer 636, a fifth layer 638, and a sixth layer 640. The first cross-section 603 is taken along the z-x plane and along a material of the first layer 602. The first layer 602, third layer 634, and fifth layer 638, which may be aligned with one another, do not include voids in the first cross-section 603. In the second layer 604, in alignment with the fourth layer 636 and the sixth layer 640, a first void 642 of the second set of voids 608 is adjacent to a second void 644 of the second set of voids. The second void 644 has a narrower width 646 in the first cross-section 603 than a width 648 of the first void 642.

Similarly, in the second cross-section 605, also taken along the z-x plane and along a material of the second layer 604, a width 650 of a first void 652 of the first set of voids 606 of the first layer 602 is wider than a width 654 of a second void 656 of the first set of voids 606 of the first layer 602. The difference in widths of the voids in the first cross-section 603 and second cross-section 605 results from the triangular geometry of the first set of voids 606 and the second set of voids 608. The triangular geometry may also drive irregularity in a geometry of cellular shape in the fourth meta-structure 626.

A first cell 658 and a second cell 660 of the cells 632 of the fourth meta-structure 626 are shown in FIG. 6D in the third cross-section 607 of the fourth meta-structure 626, taken along a plane perpendicular to the first cross-section 603 and the second cross-section 605. The first cell 658 and the second cell 660 may extend linearly through an entire thickness 662 of the fourth meta-structure 626. The cells 632 may be formed from overlapping portions of the voids of the fourth meta-structure 626. For example, the first void 652 of the first layer 602 may overlap with the second void 644 of the second layer 604 along the z-axis, the overlapping portions of both voids included in the first cell 658.

The triangular shape of the voids may result in irregular and variable dimensions and geometries of the cells 632. As an example, a width 664 of the first cell 658 is wider than a width 666 of the second cell 660. Other cells 632 of the fourth meta-structure may have different widths than the first cell 658 or the second cell 660. Furthermore the misalignment of the layers of the fourth meta-structure 626 may position each void of each layer to overlap with and be fluidly coupled to six voids in a layer above and six voids in a layer below. The fourth meta-structure 626 may have a higher degree of overlap and interlinking of voids between layers than any of the previous meta-structures shown in FIGS. 3A-5C.

Variations in cell width result in irregular cell size in a meta-structure, which may lead to variations in an acoustic wave frequency that the meta-structure may interact with. More specifically, different cell sizes may widen a range of wavelengths reflected by the meta-structure, allowing a backing with a meta-structure such as the fourth meta-structure 626 of FIGS. 6A-6D to diffuse a greater frequency bandwidth of ultrasonic waves than the meta-structures shown in FIGS. 3A-5C. The diffusion bandwidth of the backing may additionally or alternatively be augmented by varying thicknesses of the layers of the meta-structure.

Figure 7A:
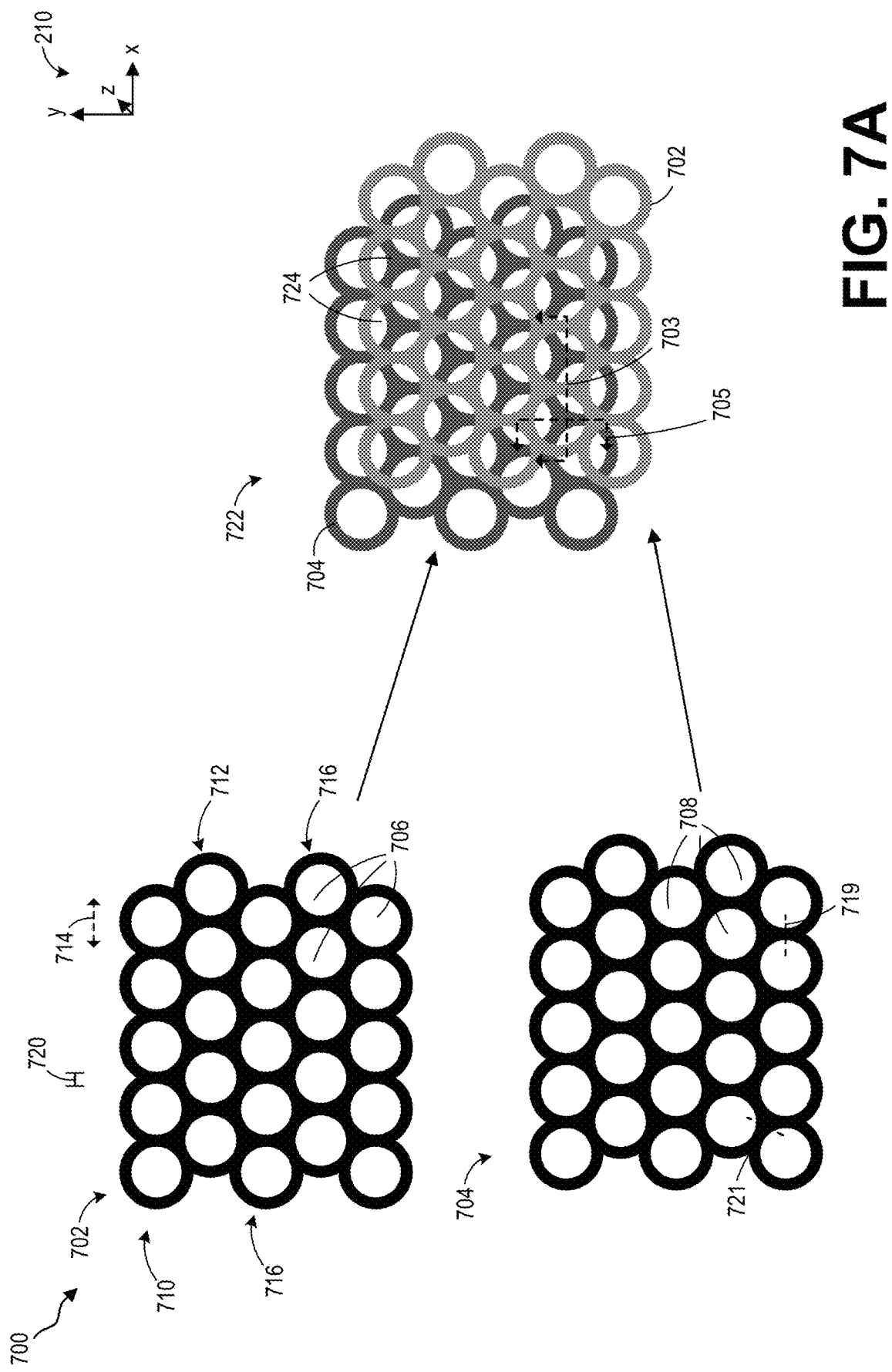
FIG. 7A shows an example of a fifth tessellation pattern for a backing material of an ultrasound probe.

A number of directions in which ultrasonic waves generated by a piezoelectric crystal may be reflected may be further increased by adapting a meta-structure of a backing material with a tessellated pattern of circular voids. An example of a fifth tessellation pattern 700 is shown in FIG. 7A. The fifth tessellation pattern 700 has a first layer 702 and a second layer 704 that are identical. Along the x-axis, a first set of voids 706 of the first layer 702 and a second set of voids 708 of the second layer 704 may be arranged in linear rows, spaced apart by a material of the first layer 702 and a material of the second layer 704.

The rows of the voids in each layer may be aligned in a manner to minimize formation of gaps between the voids. For example, a first row 710 of the first set of voids 706 in the first layer 702 is positioned immediately above, with respect to the y-axis, a second row 712 of the first set of voids 706. The second row 712 is offset from the first row 708 along the x-axis by half of a diameter 714 of the first set of voids 706. A third row 716, positioned directly below the second row 712, relative to y-axis, is aligned with the first row 710 and a fourth row 718, positioned directly below the third row 716, is aligned with the second row 712. In this way, rows of the first layer 702 and the second layer 704 alternate in alignment so that a row of the first set of voids 706 is offset from a row of the first set of voids 706 above and a row of the first set of voids 706 below and aligned with every other row of the first set of voids 706.

A line width 720 of the material of the first layer 702 and the material of the second layer 704 may not be uniform across the first layer 702 or the second layer 704. The line width 720 may be narrower in regions between two adjacent voids, as indicated by dashed line 719 spanning across two voids of the second set of voids 708 in the second layer 704, than intersecting regions between three voids, as indicated by dashed line 721 spanning across a thicker region of the material of the second layer 704. Varying the line width 720 may allow the material of the first layer 702 to fill in any spaces between voids of the first set of voids 706 and the material of the second layer 704 to fill in any spaces between the voids of the second set of voids 708 that may result from the circular geometry of the voids.

Figure 7C:
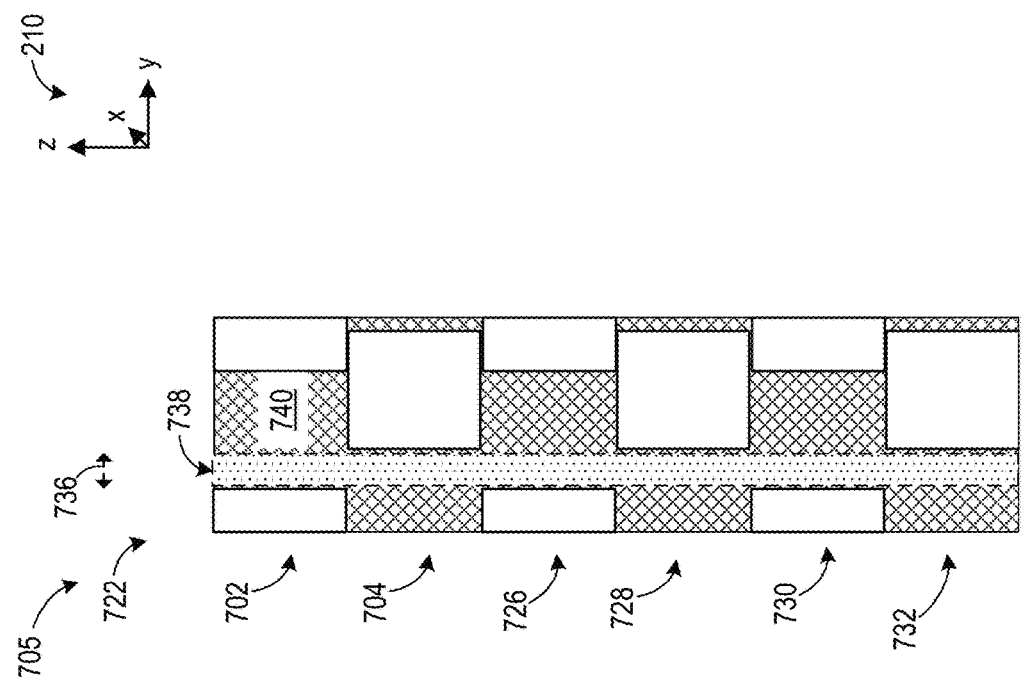
FIG. 7C shows a second cross-section of the fifth tessellation pattern.
Figure 7B:
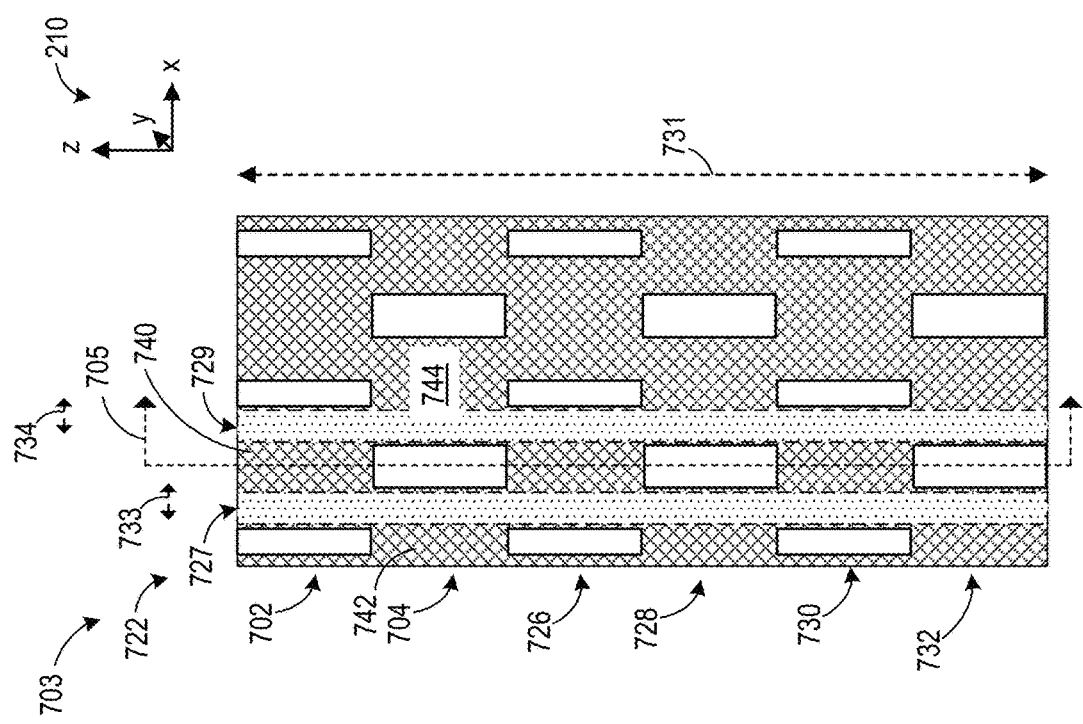
FIG. 7B shows a first cross-section of the fifth tessellation pattern.

A fifth meta-structure 722 may be formed by stacking the first layer 702 on top of the second layer 704, with respect to the z-axis. The first layer 702 and second layer 704 may be repeatedly stacked in an alternating order until the fifth meta-structure 722 achieves a desired thickness. The first layer 702 may be stacked over the second layer 704 so that the first set of voids 706 of the first layer 702 are not aligned with the second set of voids 708 of the second layer 704. Instead, each void of the first set of voids 706 of the first layer 702 may be positioned over a region of the second layer 704 where three of the second set of voids 708 intersect. A resulting geometry of cells 724 of the fifth meta-structure 722 is shown in a first cross-section 703 in FIG. 7B and a second cross-section 705 in FIG. 7C. The fifth meta-structure 722 is shown in FIGS. 7B and 7C as a stack of layers including the first layer 702, the second layer 704, a third layer 726, a fourth layer 728, a fifth layer 730, and a sixth layer 732. The first layer 702, the third layer 726, and the fifth layer 730 may be aligned along the z-axis and the second layer 704, the fourth layer 728, and the sixth layer 732 may be aligned along the z-axis. A first cell 726 and a second cell 729 of the cells 724 may extend linearly through an entire thickness 731 of the fifth meta-structure 722. A width 733 of the first cell 727 may be equal to a width 734 of the second cell 729 and may also be equal to a width 736 of a third cell 738 shown in the second cross-section 705 in FIG. 7C.

Each of the cells 724 may include overlapping portions of voids of the layers. For example, a first void 740 of the first set of voids 706 of the first layer 702 may overlap with a first void 742 of the second set of voids 708 of the second layer 704 as well as a second void 744 of the second set of voids 708 of the second layer 704. A first portion of the first void 740 of the first layer 702 that overlaps with the first void 742 of the second layer 704 below is included in the first cell 727 and a second portion of the first void 740 of the first layer 702 that overlaps with the second void 744 of the second layer 704 below is included in the second cell 729. Each void of the layers of the fifth meta-structure 722 has a first portion that is included in a first cell and a second portion that is included in a second cell.

A spacing between adjacent cells 724 of the fifth meta-structure 722 may vary due to the non-uniform line width of the first layer 702 and the second layer 704 as shown in FIG. 7A. As an example, the cells 724 shown in FIG. 7B (e.g., the first cell 727 and the second cell 729) may be spaced apart by a uniform distance that is narrower than a spacing between the third cell 738 shown in FIG. 7C and adjacent cells (not shown). Furthermore, each void of each layer may overlap and be fluidly coupled to three voids in the layer above and three voids in the layer below. The fifth meta-structure 722 may have a more complex configuration than the meta-structures shown in FIGS. 3A-6D.

The complex geometry of the fifth meta-structure 722 may result in infinite scattering of ultrasonic waves by the fifth meta-structure 722 so that the waves are reflected in all directions. The fifth meta-structure 722 may be a better diffusor of ultrasonic signals than the meta-structures shown in FIGS. 3A-6D by increasing a minimum path length of reflected waves. An efficient acoustic diffusion provided by the fifth meta-structure 722 may increase acoustic attenuation of a backing material incorporating the fifth meta-structure 722 and reduce generation of specular reflections and artifacts.

An effect of a circular tessellation pattern on reflection of ultrasonic waves may be combined with adjustment of acoustic impedance of a backing material. An example of a sixth tessellation pattern 800 is depicted in FIG. 8A, the sixth tessellation pattern 800 also comprising circular voids in a first layer 802 and a second layer 804. The first layer 802 and the second layer 804 may be identical.

Within the first layer 802, a first set of voids 806 are arranged in linear rows along the x-axis. Similarly, a second set of void 808 are also arranged in linear rows in the second layer 804. Unlike the fifth tessellation pattern 700 of FIG. 7, the first set of voids 806 and the second set of voids 808 may also be arranged in linear columns, along the y-axis. As a result of the linear alignment of the first set and second set of voids 806, 808, diagonally adjacent voids may be spaced further apart than in the fifth tessellation pattern 700 of FIG. 7A. Also in contrast to the fifth tessellation pattern 700, a line width 810 of the sixth tessellation pattern 800 may be uniform across a material of the first layer 802 and a material of the second layer 804.

As a result of the uniform line width 810 and the greater spacing between diagonally adjacent voids, the sixth tessellation pattern 800 may include a first set of pores 812 in the first layer 802, disposed in regions where four voids of the first set of voids 806 intersect. Similarly, the second layer 804 has a second set of pores 814, identical to the first set of pores 812, disposed in intersections of four voids of the second set of voids 808. Like the voids, the first set of pores 812 and the second set of pores 814 may be through holes in the material of the first layer 802 and the material of the second layer 804, set in a regular, repeating pattern. A shape of the first set of pores 812 and the second set of pores 814 may resemble a diamond with inwardly curving sides. A width 816 of the pores may be smaller than a diameter 818 of the voids.

The first layer 802 may be stacked on top of the second layer 804 to form a sixth meta-structure 820. The first layer 802 and second layer 804 may be stacked in an alternating scheme until a desired thickness of the sixth meta-structure 820 is obtained, forming cells 822 that extend through the thickness of the sixth meta-structure 820. The first layer 802 may be offset in alignment from the second layer 804 so that the first set of voids 806 of the first layer 802 do not align with the second set of voids 808 of the second layer 804. Similar to the fifth meta-structure 722 of FIG. 7, the first layer 802 may be positioned over the second layer 804 so that each void of the first set of voids 806 of the first layer 802 is centered over a pore of the second set of pores 814 of the second layer 804. Each pore of the first set of pores 812 is centered within a void of the first set of voids 806 of the first layer 802.

The misalignment of the layers of the sixth meta-structure 820 may result in non-uniform cell sizes. An arrangement of the layers of the sixth meta-structure 820 is shown in a first cross-section 803 in FIG. 8B and a second cross-section 805 in FIG. 8C. The sixth meta-structure 820 may be a stack of layers including the first layer 802, the second layer 804, a third layer 824, a fourth layer 826, a fifth layer 828, and a sixth layer 830. The first layer 802, third layer 824, and fifth layer 828 may be aligned along the z-axis while the second layer 804, fourth layer 826, and sixth layer 830 may be aligned along the z-axis.

In the first cross-section 803, first cell 832 and a second cell 834 of the cells 822 may extend linearly through an entire thickness 836 of the sixth meta-structure 820. A width 838 of the first cell 832 may be similar to a width 840 of the second cell 834 and may be defined by the width 816 of the second set of pores 814. For example, an entire width, defined along the x-axis, of a first pore 842 of the second set of pores 814 of the second layer 804 may be included in the first cell 832. The first cell 832 may also include a portion of a first void 844 of the first set of voids 806 of the first layer 802 that overlaps with the first pore 842 of the second layer 804 along the z-axis. Each void of the first layer 802, third layer 824, and fifth layer 828 may be centered over a pore in each of the second layer 804, fourth layer 826 and sixth layer 830, respectively, along the cells 822.

The first cross-section 803 may slice across a central portion of the second set of pores 814 of the second layer 804. The second cross-section 805 may be taken along a same plane as the first cross-section 803 but slicing in between the second set of pores 814 of the second layer 804 as well as between the first set of pores 812 of the first layer 802, along the x-axis. In the second cross-section 805, a third cell 846 and a fourth cell 848 of the cells 822 may extend linearly through the thickness 836 of the sixth meta-structure 820. A width 850 of the third cell 846 may be similar to or different than a width 852 of the fourth cell 848. Both the width 850 of the third cell 846 and the width 852 of the fourth cell 848 may be narrower than the width 838 of the first cell 832 and the width 840 of the second cell 834.

The widths of the third cell 846 and the fourth cell 848 may be defined by an alignment of voids in adjacent layers of the sixth meta-structure 820.

For example, the width 850 of the third cell 846 may defined by a first portion of a second void 854 of the first set of voids 806 in the first layer 802 that overlaps with a portion of a first void 856 of the second set of voids 808 in the second layer 804 below. The width 852 of the fourth cell 848 may be defined by a second portion of the second void 854 of the first layer 802 that overlaps with a portion of a second void 858 of the second layer 804. Each void of each layer may have one portion that is included in one cell and another portion that is included in a second cell. Similar to the fifth meta-structure 722 of FIGS. 7A-7C, each void of each layer of the sixth meta-structure 820 may overlap with and be fluidly coupled to four voids in a layer above and four voids in a layer below as well as to a pore of the layer above and a pore of the layer below. The sixth meta-structure 820 may have a complex configuration that also reflects acoustic waves in all directions, increasing a frequency bandwidth of diffusion more than the meta-structures of FIGS. 3A-6D. However, the varying cell widths of the sixth meta-structure 820 also results in varying cell sizes, which may further enhance a diffusivity of the sixth meta-structure 820 compared to the fifth meta-structure 722 of FIGS. 7A-7C.

By additively manufacturing a meta-structure of a backing material, such as the meta-structures shown in FIGS. 3A-8C, a printing system used to fabricate the meta-structure may be adapted with a simple set of instructions to alternate between printing a first layer of the meta-structure and a second layer of the meta-structure. The set of instructions may include a command to offset the first and second layers so that voids of the layers do not align. An acoustic impedance, a diffusion bandwidth, and an acoustic attenuation of the backing materials for an ultrasound probe may be readily adjusted by varying a geometry of the meta-structure of the backing material and a thickness of the layers. For example, the acoustic impedance may be modified to match that of a piezoelectric crystal producing ultrasonic waves by varying a line width of one of the layers or forming irregular cells, thereby adjusting a cellular volume fill ratio in the meta-structure and a density of the meta-structure, as shown by the second meta-structure 414 of FIGS. 4A-4C. The diffusion bandwidth may be enhanced by incorporating a tessellated pattern that results in irregular cell geometries, as shown in FIGS. 6A-8C, increasing reflection of ultrasonic waves in different directions. Irregular cell geometries may also be associated with more complex cell geometries, resulting in a higher attenuation coefficient of the meta-structure.

While the meta-structures shown in FIGS. 3A-8C show the meta-structures formed from tessellated patterns that are used in both the repeating first and second layers, it will be appreciated that the examples shown are non-limiting examples. Other examples of additively manufactured meta-structures for ultrasound probe backings may include layers of non-uniformly repeating or random patterns of geometric shapes with varying line widths. Additionally or alternatively, the first layer may be based upon a different shape or pattern than the second layer. Various combinations of patterns and shapes have been contemplated to impart the backing of the ultrasound probe with specific, desirable acoustic properties that may be easily adjusted during fabrication of the meta-structure by additive manufacturing.

A method 900 for fabricating a backing for an ultrasound probe is shown in FIG. 9. The backing includes a first component that is a meta-structure providing a structural framework for the backing and a second component filling cells and voids of the meta-structure. A system used to manufacture the backing may include a 3D printing device, which may be operatively/communicatively coupled to a printer-interfacing computing device, a device for filling the meta-structure with the second component, which may be a resin, as well as a device for installing the backing into a housing of the ultrasound probe. At 902, the method includes obtaining or generating a first 3D model of the first layer of the meta-structure and a second 3D model of the second layer of the meta-structure. The models of the meta-structure may be computer aided design (CAD) files, additive manufacturing files (AMF), or other 3D modeling files. The 3D models of the meta-structure may be generated on the printer-interfacing computing device. In some examples, the 3D models may be generated entirely from operator instructions via the CAD or other program. In other examples, the 3D models may be generated at least in part form information received from a 3D scanner (e.g., a laser scanner) that may image a physical model of the meta-structure. The 3D models may define the dimensions of the first and second layers, tessellation pattern of voids in a material of the first and second layers, and material properties of the first and second layers, thereby fully representing, in a digital format, the final form of the first and second layers of the meta-structure that will be produced. As appreciated by FIGS. 3A-8C, the meta-structure includes voids (e.g., empty space) and thus the 3D models of the first and second layers may include support structures, fill material, or other features that allow for printing over the voids. The 3D models may include the tessellation pattern for the first and second layers and the resin used to fill the cells and voids of the layers in order to produce a complete backing that includes the meta-structure integrated with the resin. In other embodiments, the tessellated layers may be printed separately and then filled with the resin, and thus the filling of the meta-structure with the resin may be not be included in the 3D models.

At 904, a total number of material layers of the meta-structure to be printed is obtained. In one example, the total number of layers may be determined based on a target thickness of the backing. The desired thickness may be entered by an operator or generated on the printer-interfacing computing device. The printer-interfacing computing device may compute the number of layers based on the backing thickness and a thickness of each of the layers, as the thickness of each of the layers in a range from 50 to 400 μm. In other examples, the total number of layers may be specified by a user.

As another example, a 3-D mechanical CAD model of the meta-structure, such as a brick-shaped model, may be input. The mechanical model may also be a custom shape adjust to match a specific application to provide desired shapes, attachments, etc. A machine model for the printer may be derived from the 3-D mechanical CAD model, generating "sliced" data from the 3-D CAD model by turning a solid body into a sequence of two dimensional planes. A tessellation pattern constraint may be provided during generation of "sliced" data or in the prior 3-D CAD model.

At 906, one or more 2D slices of the first model of the first layer are generated and saved in memory as a first set of instructions. The first set of instructions may be saved in memory of the printer-interfacing computing device or in memory of the printing device. The slices may be generated on the printer-interfacing computing device and then the slices are sent to the printing device as an STL file, or the first model of the first layer may be sent to the printing device, and the printing device may slice the first model into the one or more slices to generate an STL file. In doing so, the first model is sliced into one or more horizontal layers of a suitable thickness, such as a thickness in a range from 0.1 mm to 0.4 mm. Because the final thickness of the first layer may be in a range of 50-400 μm, in some examples, the first model of the first layer may act as a 2D slice and only one layer may be printed to form the first layer.

At 908, one or more 2D slices of the second model of the second layer are generated and saved in memory as a second set of instructions. The second set of instructions may be saved in memory of the printer-interfacing computing device (e.g., as an STL file) or in memory of the printing device, similar to the first set of instructions discussed above. In doing so, the second model is sliced into one or more horizontal layers of a suitable thickness, such as a thickness in a range from 0.1 mm to 0.4 mm. Because the final thickness of the second layer may be in a range of 50-400 μm, in some examples, the second model of the second layer may act as a 2D slice and only one layer may be printed to form the second layer.

At 910, method 900 includes printing the first layer according to the first set of instructions. The first layer may be printed on a build layer or other suitable structure. The first layer may be printed with a repeating pattern, e.g., the tessellation pattern of voids, as explained above. The first layer is printed with the printing device, which may be a suitable device configured to print metal, ceramic, and/or other materials with high thermal conductivity. The printing device may utilize selective laser melting (SLM) technology, direct metal laser sintering (DMLS) technology, or other suitable metal or ceramic printing technology. In examples where the voids are initially filled with a resin, the printing device may be configured to print multiple materials (e.g., the metal and the resin) and thus may include more than one print head.

During printing, the print head(s) is moved, in both horizontal and vertical directions, to complete or print each layer of the 3D model, by a controlled mechanism that is operated by control software running on the printing device, e.g., a computer-aided manufacturing (CAM) software package adapted for use with the printing device. The build plate is typically stationary with its upper planar surface parallel to a horizontal plane, although in some examples the build plate may be moved up and down vertically. The printed material solidifies to form a layer (and to seal together layers of the meta-structure), and the print head or build plate is then moved vertically prior to starting the printing of the next layer.

At 912, the second layer is printed according to the second set of instructions. The second layer is printed after the first layer has been printed, and is printed on top of the first layer. In some examples, the second set of instructions may dictate that the second layer be printed offset from the first layer, as shown in FIG. 3A and discussed above, for example. The second layer may be the same or different from the first layer in line thickness, layer thickness, or geometry, also printed as a layer material with a tessellation pattern of voids, as dictated by the second set of instructions.

At 914, a next layer of the meta-structure is printed according to the first set of instructions. The next layer printed according to the first set of instructions is printed on the last layer printed (e.g., on the second layer) and is aligned with the first layer. At 916, a next layer is printed according to the second set of instructions. The next layer printed according to the second set of instructions is printed on the last layer printed and is aligned with the second layer.

At 918, method 900 determines if the total number of layers of the meta-structure has been printed. If the total number of layers has not been printed, method 900 loops back to 914 and prints the next layer according to the first set of instructions. In this way, the printing device proceeds to print successive layers of the meta-structure, alternating between printing a layer according to the first of instructions and printing a layer according to the second set of instructions, until the entire meta-structure is created.

If the total number of layers has been printed, method 900 proceeds to 920 to add the resin to the complete meta-structure in order to form a backing material. The resin may be added by an external device, such as an injector, allowing the resin to flow into the meta-structure and fill the cells and voids of the meta-structure to form the backing. Alternatively, the meta-structure may be printed with the resin integrated into the meta-structure, and thus in some examples the separate step of adding the resin may be dispensed with. The resin may be cured by exposure to heat or UV radiation and allowed to harden. At 922, the backing material is installed in an acoustic stack or other structure of an ultrasound probe or other suitable acoustic probe. Another external device such as an automaton, or alternatively an operator, may install the backing into the probe. The backing may be inserted into an outer housing of the ultrasound probe, behind an element of the probe that generates ultrasonic signals.

Thus, method 900 provides for 3D printing of a meta-structure adapted to be a component in a backing of an ultrasound probe. In other examples, however, the meta-structure may be formed instead by stack lamination. In such an example, multiple copies of each of the first and second layers of the meta-structure may be formed independently by a process such as photolithography, and the layers may be stacked in an alternating arrangement and laminated to fuse the layers together. As another example, a complete structure of the meta-structure may be printed and impregnated with resin. The impregnated structure maybe machined and coupled to other components of the ultrasound probe by laminating or some other method.

In this way, a backing of an acoustic probe, such as an ultrasound probe, may be fabricated via a cost-effective method that readily allows for tuning of a backing material to enhance acoustic properties of the backing. A meta-structure of the backing material provides acoustic diffusion, impedance, thermal conductivity, and mechanical strength, and may be additively manufactured by repeatedly stacking a first layer and a second layer in an alternating regime. Each of the first layer and the second layer may be a layer of material with voids arranged in a tessellation pattern and stacked so that the second layer is offset from the first layer and the voids of the first and second layers are not aligned. Cells of the meta-structures may have physical variables such as geometry, size, fill ratio, and volume that depend on a shape of the voids and the offset alignment of the layers. The physical variables moderate acoustic properties of the meta-structure, allowing the acoustic properties to be easily adjusted by varying a shape, layer thickness, and/or stacking alignment of the first and second layers. A data set for printing and tuning the meta-structure may demand a relatively small amount of storage in a memory of an additive manufacturing system controller, such as a computer in communication with a 3D printer. The data set may be a file adapted with instructions for printing two layers with adjustable parameters for the geometry of the tessellated pattern and the stacking alignment. A demand on the controller's memory may be minimized, decreasing an amount of time for the controller to access and execute the instructions for printing the meta-structure.

A technical effect of additively manufacturing a meta-structure for an ultrasound probe backing as alternating, staggered layers of a tessellated pattern is that an acoustic diffusivity, impedance and attenuation of a backing material incorporating the meta-structure is increased.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

In one embodiment, an ultrasound transducer includes an element for generating ultrasonic waves and a backing arranged behind the element, the backing including a layer having a tessellation pattern. In a first example of the ultrasound transducer, the backing comprises a meta-structure including the layer and a fill material filling cells of the meta-structure. A second example of the ultrasound transducer optionally includes the first example, and further includes, wherein the meta-structure is more rigid and porous than the fill material and is formed from a thermally conductive and acoustically diffusing material, and wherein the fill material is configured to attenuate acoustic waves. A third example of the ultrasound transducer optionally includes one or more of the first and second examples, and further includes, wherein the layer is a first layer and the backing further comprises a plurality of additional layers including a first set of layers aligned with the first layer and a second set of layers offset from the first layer, each layer of the plurality of additional layers including the tessellation pattern. A fourth example of the ultrasound transducer optionally includes one or more of the first through third examples, and further includes, wherein the first layer and plurality of additional layers form openings that extend through a thickness of the plurality of layers, the openings defined by the tessellation pattern of each layer. A fifth example of the ultrasound transducer optionally includes one or more of the first through fourth examples, and further includes, wherein the tessellation pattern is a repeating pattern of circular voids. A sixth example of the ultrasound transducer optionally includes one or more of the first through fifth examples, and further includes, wherein the tessellation pattern is a repeating pattern of hexagonal voids. A seventh example of the ultrasound transducer optionally includes one or more of the first through sixth examples, and further includes, wherein the tessellation pattern is a repeating pattern of triangular voids. An eighth example of the ultrasound transducer optionally includes one or more of the first through seventh examples, and further includes, wherein the tessellation pattern is a repeating pattern of square voids. A ninth example of the ultrasound transducer optionally includes one or more of the first through eighth examples, and further includes, wherein the first set of layers have a different line width of a material defining the tessellation pattern than a line width of a material defining the tessellation pattern of the second set of layers.

In another embodiment, a method includes additively manufacturing a layered meta-structure, at least a first layer of the meta-structure having a tessellation pattern, filling the layered meta-structure with a resin to form the backing material, and coupling the backing material in an acoustic stack of the acoustic probe. In a first example of the method, additively manufacturing the layered meta-structure includes printing the first layer. A second example of the method optionally includes the first examples, and further includes wherein printing the first layer includes, with an additive manufacturing system controller, retrieving a first set of instructions stored in a memory of the system controller and executing the first set of instructions to print the first layer. A third example of the method optionally includes one or more of the first and second examples, and further includes, wherein additively manufacturing the layered meta-structure includes printing a second layer on top of the first layer, the second layer having the tessellation pattern. A fourth example of the method optionally includes one or more of the first through third examples, and further includes, wherein printing the second layer includes, with the system controller, retrieving a second set of instructions stored in a memory of the system controller and executing the second set of instructions to print the second layer. A fifth example of the method optionally includes one or more of the first through fourth examples, and further includes, wherein printing the second layer on top of the first layer includes printing the second layer offset in alignment from the first layer. A sixth example of the method optionally includes one or more of the first through fifth examples, and further includes, wherein additively manufacturing the layered meta-structure includes printing a plurality of additional layers, the plurality of additional layers including a first set of layers having the tessellation pattern and printed to align with the first layer and a second set of layers having the tessellation pattern and printed to align with the second layer, each layer of the first set of layers alternating along a vertical axis with a respective layer of the second set of layers. A seventh example of the method optionally includes one or more of the first through sixth examples, and further includes, wherein printing the plurality of additional layers comprises; for each layer of the first set of layers, retrieving the first set of instructions stored in the memory of the system controller and executing the first set of instructions to print that layer, and for each layer of the second set of layers, retrieving the second set of instructions stored in the memory of the system controller and executing the second set of instructions to print that layer. An eighth example of the method optionally includes one or more of the first through seventh examples, and further includes, wherein the tessellation pattern comprises a repeating pattern of voids having a geometric shape, each void uniformly spaced away from and uniformly aligned with adjacent voids.

In another embodiment, a backing material includes a resin and a meta-structure formed from a plurality of layers each having a tessellation pattern of voids, the meta-structure filled with the resin and configured to diffuse and attenuate acoustic waves generated within the acoustic probe.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An ultrasound transducer, comprising:
an element for generating ultrasonic waves; and
a backing arranged behind the element, the backing comprising a meta-structure formed from a plurality of stacked, tessellated layers, with each layer defining a tessellation pattern of voids and each layer stacked directly upon another, wherein the tessellation pattern is a repeating geometric shape that covers a plane without presence of interstices between adjacent shapes of the repeating geometric shape, and wherein the voids defined by the meta-structure are filled with a fill material and the meta-structure is configured to diffuse and attenuate acoustic waves.

2. The ultrasound transducer of claim 1, wherein the meta-structure is more rigid and porous than the fill material and is formed from a thermally conductive and acoustically diffusing material, and wherein the fill material is configured to attenuate acoustic waves.

3. The ultrasound transducer of claim 1, wherein the plurality of layers includes a first layer and a plurality of additional layers including a first set of layers aligned with the first layer and a second set of layers offset from the first layer.

4. The ultrasound transducer of claim 3, wherein the voids extend through a thickness of the plurality of layers.

5. The ultrasound transducer of claim 4, wherein the tessellation pattern is a repeating pattern of circular voids.

6. The ultrasound transducer of claim 3, wherein the first set of layers have a different line width of a material defining the tessellation pattern than a line width of a material defining the tessellation pattern of the second set of layers.

7. The ultrasound transducer of claim 1, wherein the tessellation pattern is a repeating pattern of hexagonal voids.

8. The ultrasound transducer of claim 1, wherein the tessellation pattern is a repeating pattern of triangular voids.

9. The ultrasound transducer of claim 1, wherein the tessellation pattern is a repeating pattern of square voids.

10. A backing material for an acoustic probe, comprising:
a resin; and
a meta-structure formed from a plurality of stacked, tessellated layers, with each layer defining a tessellation pattern of voids and each layer stacked directly upon another, wherein the tessellation pattern is a repeating geometric shape that covers a plane without presence of interstices between adjacent shapes of the repeating geometric shape, and wherein the voids defined by the meta-structure are filled with the resin and the meta-structure is configured to diffuse and attenuate acoustic waves generated within the acoustic probe.

* * * * *